US007220896B2

(12) United States Patent
Henkes et al.

(10) Patent No.: US 7,220,896 B2
(45) Date of Patent: May 22, 2007

(54) PYROPHOSPHATASE STRESS-RELATED PROTEINS AND METHODS OF USE IN PLANTS

(75) Inventors: Stefan Henkes, Potsdam (DE); Ruoying Chen, Apex, NC (US); Nocha van Thielen, Chapel Hill, NC (US); Oswaldo da Costa e Silva, Apex, NC (US)

(73) Assignee: BASF Plant Science GmbH, Ludwigshafen (DE)

( * ) Notice: Subject to any disclaimer, the term of this patent is extended or adjusted under 35 U.S.C. 154(b) by 181 days.

(21) Appl. No.: 10/169,045

(22) PCT Filed: Dec. 22, 2000

(86) PCT No.: PCT/US00/35100

§ 371 (c)(1),
(2), (4) Date: Nov. 18, 2002

(87) PCT Pub. No.: WO01/45494

PCT Pub. Date: Jun. 28, 2001

(65) Prior Publication Data

US 2004/0055032 A1    Mar. 18, 2004

(51) Int. Cl.
C12N 15/82 (2006.01)
C12N 15/29 (2006.01)
(52) U.S. Cl. .................. 800/289; 536/23.6; 435/320.1; 435/468
(58) Field of Classification Search ................ 800/289; 435/468; 536/23.6
See application file for complete search history.

(56) References Cited

FOREIGN PATENT DOCUMENTS

| EP | 0/485044 A2 | 4/1991 |
|---|---|---|
| WO | WO 01/33945 A1 | 5/2001 |

OTHER PUBLICATIONS

Sarafian V. et al. Molecular cloning and sequence of cDNA encoding the pyrophosphate-energized vacuolar membrane proton pump of Arabidopsis thaliana. Proc Natl Acad Sci U S A. Mar. 1, 1992;89(5):1775-9.*
Doerks T. et al. Protein annotation: detective work for function prediction. Trends Genet. Jun. 1998;14(6):248-50.*
Broun P et al. Catalytic plasticity of fatty acid modification enzymes underlying chemical diversity of plant lipids. Science. Nov. 13, 1998;282(5392):1315-7.*
Van Camp W. et al. Enhancement of oxidative stress tolerance in transgenic tobacco plant overproducing Fe-superoxide dismutase in chloroplasts. Plant Physiol. Dec. 1996;112(4):1703-14.*
Sandler S.J. et al. Inhibition of gene expression in transformed plants by antisense RNA. Plant Molecular Biology, 1988, vol. 11 No. 3, pp. 301-310.* van der Krol A.R. et al. Inhibition of flower pigmentation by antisense CHS genes: promoter and minimal sequence requiremen for the antisense effect. Plant Mol Biol. Apr. 1990;14(4):457-66.*
Waterhouse et al. Virus resistance and gene silencing: killing the messenger. Trends Plant Sci. Nov. 1999;4(11):452-457.*
Gdula D.A. et al. GenBank Accession No. AF085601, Drosophila melanogaster inorganic pyrophosphatase NURF-38 (Nurf-38 mRNA, complete cds, Dec. 18, 1998.*
Minami A. et al. Abscisic acid-induced freezing tolerance in the moss Physcomitrella patens is accompanied by increased expression of stress-related genes. J Plant Physiol. May 2003;160(5):475-83.*
Badur et al., "Induction of pathogenis-related proteins in sugar accumulating tobacco leaves", 1994, Photosynthetica 30(4):575-582.
Bohnert and Jensen, "Strategies for engineering water-stress tolerance in plants", 1996, Trends in Biotech., 14:89-97.
Carystinos et al., "Vacuolar H+-Translocating Pyrophosphatase Is Induced by Anoxia or Chilling in Seedlings of Rice", 1995, Plant Physiol., 108:641-649.
Colombo and Cerana, "Enhanced Activity of Tonoplast Pyrophosphatase in NaCl-Grown Cells of Daucus carota", 1993, J. Plant Physiol., vol. 142, pp. 226-229.
Gaxiola et al., "The Arabidopsis thaliana proton transporters, AtNhxl and Avpl, can function in cation detoxification in yeast", 1999, Proc. Natl. Acad. Sci, vol. 96, pp. 1480-1485.
Groves, J.T., "Peroxynitrite: reactive, invasive and enigmatic", 1999, Curr. Opin. Chem. Biol. 3(2):226-235.
Haertel et al., "DGD1-independent biosynthesis of extraplastidic galactolipids after phosphate deprivation in Arabidopsis", 2000, Proc. Natl. Acad. Sci., 97:10649-10654.
Jelitto et al., "Inorganic pyrophosphate content and metabolites in potato and tobacco plants expressing E. coli pyrophosphatase in their cytosol", 1992, Planta 188:238-244.
Lerchl et al., "Impaired Photoassimilate Partitioning Caused by Phloem-Specific Removal of Pyrophosphate Can Be Complemented by a Phloem-Specific Cytosolic Yeast-Derived Invertase in Transgenic Plants", 1995, Plant Cell 7:259-270.

(Continued)

*Primary Examiner*—Cynthia Collins
(74) *Attorney, Agent, or Firm*—Elaine Sale; Mark Westhafer; Ruoying Chen

(57) ABSTRACT

A transgenic plant transformed by a pyrophosphatase stress-related protein (PPSRP) coding nucleic acid, wherein expression of the nucleic acid sequence in the plant results in increased tolerance to environmental stress as compared to a wild type variety of the plant. Also provided are agricultural products, including seeds, produced by the transgenic plants. Also provided are isolated PPSRP, and isolated nucleic acid coding PPSRP, and vectors and host cells containing the latter. Further provided are methods of producing transgenic plants expressing PPSRP, methods of identifying novel PPSRP, and methods of modifying the expression of PPSRP in plants.

13 Claims, 5 Drawing Sheets

OTHER PUBLICATIONS

Nakanishi and Maeshima, "Molecular Cloning of Vacuolar H+-Pyrophosphatase and Its Developmental Expression in Growing Hypocotl of Mung Bean", 1998, Plant Physiol. 116:589-597.

Paul et al., "Transgenic tobacco plants with strongly decreased expression of pyrophosphate: Fructose-6-phosphate 1-phosphotransferase do not differ significantly from wild type in photosynthate partitioning, plant growth or their ability to cope with limiting phosphate, limiting nitrogen and suboptimal temperatures," 1995, Planta 196:277-283.

Quarrie SA, "New molecular tools to improve the efficiency of breeding for increased drought resistance", 1996, Plant Growth Reg. 20:167-178.

Quatrano, R. et al, "gb40b06.y1 Moss EST library", Accession No. AW739302, Apr. 27, 2000.

Rea et al., "Vacuolar H+-translocating pyrophosphatases: a new category of ion translocase", 1992, Trends in Biochem. Sci. 17:348-353.

Sarafian et al., "Molecular cloning and sequence of cDNA encoding the pyrophosphate-energized vacuolar membrane proton pump of *Arabidopsis thaliana*", 1992, Proc. Natl. Acad. Sci., vol. 89, pp. 1775-1779.

Sivula et al., "Evolutionary aspects of inorganic pyrophosphatase", 1999, FEBS Letters 454:75-80.

Smirnoff, "Plant resistance to environmental stress", 1998, Curr. Opin. Plant Biotech. 9:214-219.

Stitt and Sonnewald, "Regulation of Metabolism in Transgenic Plants", 1995, Ann. Rev. Plant Physiol. Plant Mol. Biol., 46:641-368.

Stitt, "Pyrophosphate as an Energy Donor in the Cytosol of Plant Cells: an Enigmatic Alternative to ATP", 1998, Bot. Acta 111:167-175.

Weiner et al. "Subcellular compartmentation of pyrophosphate and alkaline pyrophosphatase in leaves", 1987, Biochem. Biophys. Acta 893:13-21.

Zrenner et al., "Analysis of the expression of potato uridinediphosphate-glucose pyrophosphorylase and its inhibition by antisense RNA", 1993, Planta 247-252.

* cited by examiner

FIGURE 1

Nucleotide sequence of the partial Pyrophosphatase (PPase-1) from *Physcomitrella patens* (SEQ ID NO:1)

AACACCACCCCACAGAGGAGTTCGAAGAGGAACTAAACGAGGGAAAGTTCTCCA

GCTGGAACGCTCCTCTTCACGAGGTTTGCCCATGCATTGTTGGTCTCTTCAATGAC

CTTCAGTGCATAATCCTTATCAGCAGGCTTGTTATCAAGACCAAACCTATTGGCGG

GCTTTCCATCGGGGATCTTGTAATCTCTGAACCAGTCTCTAATTGCGGTCAAAGTG

CCTGGGAAGTGCTTCTCGCAATCAGCCACGTTGTTGACCAGATCAGCCTTGGGATC

GTCGATGGAGATAGCCACAACTTTCCAGTCAAGTTCACCCTCGTCAATCATGGCTA

AAACCGCGATGGGTTTCACCTTAAGGACTTCTCCAATTTTGGCTTGCCTCTCCCCA

ATTTCAACAACGTCAACTGGGTCGTTGTCACCGAACGCGTTCTCCACGTCAGAGTT

AGAGTGCGAAGGGTCCTCCCATGTCTGGGGAAGAAGTCCGTAATTCCAGTTGATG

TTATAAGGGTAGAACCGGAGCTTCCCCTTCTTCGTGTCCTGCTTGATGGGAGTGCT

GGGCTCCTCAGTCGCAACCTCCATCTTAGCACTAGTCTCCTTAGGGATCTCAACAA

CGAAGTTGTAGAGTCCGTCTCCGGCGTGGAGGGGGATATCATGCCATGGTGAGAT

CGTCTTGCCAGACTTGTCAGAGAAGAAGACCCTGTACTCTAGAGACTCAGCTGCTC

CTTCCTCCTTGACGGTATACTCTGCAGAGACGACCTTACAGACCTGGAATCTCCTG

CTCTTCACAGCAGACCTCTGCACGAAAGATTGGTGCAGTGGGGCTGCCCTCAAGG

AGAGGGAAGCAGCAGGCAACAATGCCGTCCTCTGTGAACCCTTCACCACTGATGA

GTTCACGCACTGTGGCAAATGGGACACGCACCCTGCTGCCATAGCTCTTGCTGCCG

CCATTGTCACCTGCTGCGATGCAACCTTGCGGACACCGCACGACGAGAACTGAGA

GCACGAGAGAGCGAGCGAGAGACAGAGACGCAAGCAGATTTCGATGTCCTAGTC

CAGGACCCTCCCCGTCGGAGTTTAGTGTGTGGTGCCTGATGAACCAGTGCATCTGG

ACTCACTAAAAACGAATATGCTCCGTTTTAGTGACTTACTAATCCTAACTTACAAA

CTTTCTCGCAGCGTNCCCATGGGCCTGCTGAATGCCTAAGATGCTACGTTNCCCGT

GTGGGGAGCTCATCTGGTGC

FIGURE 2

Nucleotide sequence of the full-length PPase-1 from *Physcomitrella patens* (SEQ ID NO: 2)

GAATTCGGCACCAGGTCGTGCGGTGTCCGCAAGGTTGCATCGCAGCAGGTGACAA
TGGCGGCAGCAAGAGCTATGGCAGCAGGGTGCGTGTCCCATTTGCCACAGTGCGT
GAACTCATCAGTGGTGAAGGGTTCACAGAGGACGGCATTGTTGCCTGCTGCTTCCC
TCTCCTTGAGGGCAGCCCCACTGCACCAATCTTTCGTGCAGAGGTCTGCTGTGAAG
AGCAGGAGATTCCAGGTCTGTAAGGTCGTCTCTGCAGAGTATACCGTCAAGGAGG
AAGGAGCAGCTGAGTCTCTAGAGTACAGGGTCTTCTTCTCTGACAAGTCTGGCAAG
ACGATCTCACCATGGCATGATATCCCCCTCCACGCCGGAGACGGACTCTACAACTT
CGTTGTTGAGATCCCTAAGGAGACTAGTGCTAAGATGGAGGTTGCGACTGAGGAG
CCCAGCACTCCCATCAAGCAGGACACGAAGAAGGGGAAGCTCCGGTTCTACCCTT
ATAACATCAACTGGAATTACGGACTTCTTCCCCAGACATGGGAGGACCCTTCGCAC
TCTAACTCTGACGTGGAGAACGCGTTCGGTGACAACGACCCAGTTGACGTTGTTGA
AATTGGGGAGAGGCAAGCCAAAATTGGAGAAGTCCTTAAGGTGAAACCCATCGCG
GTTTTAGCCATGATTGACGAGGGTGAACTTGACTGGAAAGTTGTGGCTATCTCCAT
CGACGATCCCAAGGCTGATCTGGTCAACAACGTGGCTGATTGCGAGAAGCACTTC
CCAGGCACTTTGACCGCAATTAGAGACTGGTTCAGAGATTACAAGATCCCCGATG
GAAAGCCCGCCAATAGGTTTGGTCTTGATAACAAGCCTGCTGATAAGGATTATGC
ACTGAAGGTCATTGAAGAGACCAACAATGCATGGGCAAACCTCGTGAAGAGGAG
CGTTCCAGCTGGAGAACTTTCCCTCGTTTAGTTCCTCTTCGAACTCCTCTGTGGGTG
GTGTTGTTCAATCTGGCAACCAGATTACATCACAACACGATTAGCTCTTACGGAAA
CTTCAGTTTTGCTAGAGTTTAGTGTTCCAACATTTGTACCTTGTATCTCTTGGTTTCC
GAGAATTTGATAACTCCTAGAATCAATTGATTGCAGCGTAAGCAGCAGCTTTGTAA
CTTTGTGGGTCGTCATTGCATTGACCGTTCTCCTGCGAGGACAAGAGCTGTTAGAA
GTATCTTGTTGTGGTAACATGTGCCTCCCTGCAACCTAGATTCCACAGTTTGCATG

AGTCATTGATATAATGTAGCAGATTATTCCAGTGGCTTTTTGCTCGTTCGCTACAGC
GTTATCTTGAGACAGAATGATCAATCCTCTTCTTAGAACGTTAGTACTGGCTGAAC
TTGGCAATTGCTTTATTATTAAACACGTGAAGGCTTATTGCCAAGTTTATCAATAA
ACAAAGCATTGTATCCTAAAAAAAAAAAAAAAAAAAAAAAAAAAACTCGAG

FIGURE 3

Deduced amino acid sequence of PPase-1 from *Physcomitrella patens* (SEQ ID NO: 3)

MAAARAMAAGCVSHLPQCVNSSVVKGSQRTALLPAASLSLRAAPLHQSFVQRSAVK
SRRFQVCKVVSAEYTVKEEGAAESLEYRVFFSDKSGKTISPWHDIPLHAGDGLYNFVV
EIPKETSAKMEVATEEPSTPIKQDTKKGKLRFYPYNINWNYGLLPQTWEDPSHSNSDV
ENAFGDNDPVDVVEIGERQAKIGEVLKVKPIAVLAMIDEGELDWKVVAISIDDPKADL
VNNVADCEKHFPGTLTAIRDWFRDYKIPDGKPANRFGLDNKPADKDYALKVIEETNN
AWANLVKRSVPAGELSLV*

FIGURE 4

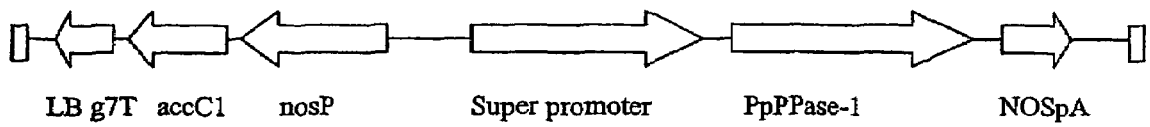

LB  g7T  accC1  nosP       Super promoter        PpPPase-1       NOSpA

PYROPHOSPHATASE STRESS-RELATED PROTEINS AND METHODS OF USE IN PLANTS

BACKGROUND OF THE INVENTION

1. Field of the Invention

This invention relates generally to nucleic acid sequences encoding proteins that are associated with abiotic stress responses and abiotic stress tolerance in plants. In particular, this invention relates to nucleic acid sequences encoding proteins that confer drought, cold, and/or salt tolerance to plants.

2. Background Art

Environmental stress causes significant crop losses. The stresses are numerous and often crop- and location-specific. They include drought, high salinity, temperature extremes, hypoxia, mineral nutrient deficiency and UV-B radiation. Research in this area is driven by the hope of improving crop yield in afflicted areas. Currently, actual but slow advances are being made by crop breeders and agronomists using tried- and tested methodology. However, biotechnology will increasingly have a role as genes involved in stress tolerance are cloned and their mode of action elucidated (Quarrie S A, 1996 Plant Growth Reg. 20:167–178). By improving a plant's performance in response to different environmental stresses, the losses in productivity and risks to farming can be greatly reduced. Modifying a plant's tolerance to environmental stresses also allows a plant to be grown in regions where a plant or plant variety is typically unable to grow (Bohnert and Jensen, 1996 TIBTECH 14:89–97).

The biochemical and physiological basis for plant stress tolerance is not well understood. However, it does appear that common damage from different stresses (drought, salt and cold stress) is mostly due to dehydration (Smirnoff, 1998 Curr. Opin. Plant Biol. 9:214–219). The response that distinguishes drought-tolerant and -sensitive species most clearly is a dramatic accumulation of osmoprotective substances and also of ions that leads to osmotic adjustments (Bohnert and Jensen 1996 TIBTECH 14:89–97).

Sucrose is an important osmoprotectant under dehydration stress conditions (water deficit and freezing stress). The biosynthesis of sucrose has several control steps (Stitt and Sonnewald, 1995 Ann. Rev. Plant Physiol. Plant Mol. Biol. 46:641–368) and pyrophosphate (PPi) metabolism plays an important role in this biosynthetic pathway (Stitt, 1998 Bot. Acta 111:167–175). PPi is mainly produced as a by-product of biosynthesis of macromolecules such as RNA, proteins and cellulose in elongating cells (Nakanishi and Maeshima, 1998 Plant Physiol. 116:589–597). There are three enzymatic activities involved in metabolizing PPi in the cytosol, two reversible reactions catalyzed by PFP (Pyrophosphate dependent Fructose-6-P Phosphofructokinase; Paul et al., 1995 Planta 196:277–283) and UGPase (UDP-Glucose Pyrophosphorylase; Zrenner et al., 1993 Planta 247–252), respectively, and the tonoplast membrane bound inorganic pyrophosphatase (PPase, Rea et al., 1992 Tr. in Biochem. 17:348–353). A soluble inorganic pyrophosphatase exists only in chloroplasts, but not in the cytosol (Weiner et al., 1987 Biochem. Biophys. Acta 893:13–21).

Two families of soluble inorganic pyrophosphatase are known to date. Family I, including most of the currently known PPases, and family II, including PPases from certain bacterial species. The two families do not show any sequence similarity to each other. In addition to soluble PPases, plants (and certain bacteria) have a membrane-bound PPase that works as a reversible pump. Membrane-bound PPases are much larger and do not have any sequence similarity to any of the two families of soluble PPase. Plant soluble PPase resemble prokaryotic PPase more closely than animal/fungal PPases (Sivual et al., 1999 FEBS Letters 454:75–80).

The ectopic expression of a soluble inorganic pyrophosphatase in the cytosol has been shown to shift carbon metabolism towards the synthesis of sucrose in the transgenic plants due to the removal of PPi as a product of the PFP and UGPase reaction. The constitutive over-expression (35S promoter) of *E. coli* soluble pyrophosphatase in the cytosol of plant cells leads to an accumulation of sucrose in the leaves of the transgenic tobacco plants (Jellito et al., 1992 Planta 188:238–244). The same effects were obtained upon expression of the enzyme only in the phloem (rolC promoter) indicating the essential role of PPi for phloem loading of sucrose (Lerchl et al., 1995 Plant Cell 7:259–270). Additionally, both the $^{35}$S- and the rolC-plants were reduced in growth. These examples show the importance of PPi for plant metabolism and growth. The alteration of the amount and/or availability of inorganic phosphate in the cell also has profound effects on plant lipid metabolism (Haertel et al., 2000 PNAS 97:10649–10654), and thereby can lead to changes in the composition of the plasmalemma as well as the organelle membranes.

The response of transgenic plants expressing a soluble inorganic pyrophosphatase in the cytosol to environmental stresses like drought, salt and freezing has not been determined thus far. Therefore what is needed is the identification of genes and proteins encoded by those genes that have pyrophosphatase-like activity and that are involved in stress tolerance in plants. Elucidating the function of genes expressed in stress tolerant plants will not only advance our understanding of plant adaptation and tolerance to environmental stresses, but also may provide important information for designing new strategies for crop improvement. Newly generated stress tolerant plants will have many advantages, such as increasing the range that crop plants can be cultivated by, for example, decreasing the water requirements of a plant species. This invention fulfills in part the need to identify new, unique pyrophosphatases capable of conferring stress tolerance to plants upon over-expression.

SUMMARY OF THE INVENTION

The present invention provides a transgenic plant transformed by a pyrophosphatase stress-related protein (PPSRP) coding nucleic acid, wherein expression of the nucleic acid sequence in the plant results in increased tolerance to environmental stress as compared to a wild type variety of the plant. The invention provides that the PPSRP can be selected from one of the well known general classes of pyrophosphatase proteins, including those known as pyrophosphatase family I and family II (PPases). The invention further provides specific examples of PPSRP, and PPSRP coding nucleic acids, such as PPase-1.

The invention provides in some embodiments that the PPSRP and coding nucleic acid are that found in members of the genus *Physcomitrella*. In another preferred embodiment, the nucleic acid and protein are from a *Physcomitrella patens*. The invention provides that the environmental stress can be salinity, drought, temperature, metal, chemical, pathogenic and oxidative stresses, or combinations thereof. In preferred embodiments, the environmental stress can be drought.

The invention further provides a seed produced by a transgenic plant transformed by a PPSRP coding nucleic acid, wherein the plant is true breeding for increased tolerance to environmental stress as compared to a wild type variety of the plant. The invention further provides a seed produced by a transgenic plant expressing a PPSRP, wherein the plant is true breeding for increased tolerance to environmental stress as compared to a wild type variety of the plant.

The invention further provides an agricultural product produced by any of the above-described transgenic plants. The invention further provides an isolated pyrophosphatase stress-related protein (PPSRP), wherein the PPSRP is as described above. The invention further provides an isolated pyrophosphatase stress-related protein (PPSRP) coding nucleic acid, wherein the PPSRP coding nucleic acid codes for a PPSRP as described above.

The invention further provides an isolated recombinant expression vector comprising a PPSRP coding nucleic acid as described above, wherein expression of the vector in a host cell results in increased tolerance to environmental stress as compared to a wild type variety of the host cell. The invention further provides a host cell containing the vector. The invention further provides a plant containing the host cell.

The invention further provides a method of producing a transgenic plant with a pyrophosphatase stress-related protein (PPSRP) coding nucleic acid, wherein expression of the nucleic acid in the plant results in increased tolerance to environmental stress as compared to a wild type variety of the plant comprising: (a) transforming a plant cell with an expression vector comprising a PPSRP coding nucleic acid, and (b) generating from the plant cell a transgenic plant with an increased tolerance to environmental stress as compared to a wild type variety of the plant. In preferred embodiments, the PPSRP is as described above. In preferred embodiments, the PPSRP coding nucleic acid is as described above.

The present invention further provides a method of identifying a novel pyrophosphatase stress-related protein (PPSRP), comprising (a) raising a specific antibody response to a PPSRP, or fragment thereof, as described above; (b) screening putative PPSRP material with the antibody, wherein specific binding of the antibody to the material indicates the presence of a potentially novel PPSRP; and (c) identifying from the bound material a novel PPSRP in comparison to known PPSRP. Alternatively, hybridization with nucleic acid probes as described above can be used to identify novel PPSRP nucleic acids.

The present invention also provides methods of modifying stress tolerance of a plant comprising, modifying the expression of a pyrophosphatase kinase stress-related protein (PPSRP) in the plant, wherein the PPSRP is as described below. The invention provides that this method can be performed such that the stress tolerance is either increased or decreased.

BRIEF DESCRIPTION OF THE DRAWINGS

FIG. 1 shows the partial cDNA sequence of PPase-1 from *Physcomitrella patens* (SEQ ID NO: 1).

FIG. 2 shows the full-length cDNA sequence of PPase-1 from *Physcomitrella patens* (SEQ ID NO: 2).

FIG. 3 shows the deduced amino acid sequence of Ppase-1 from *Physcomitrella patens* (SEQ ID NO: 3).

FIG. 4 shows a diagram of the plant expression vector pBPSMI001 containing the super promoter driving the expression of PpPPase-1. The components are: aacCI gentamycin resistance gene (Hajdukiewicz et al., 1994 Plant Molecular Biology 25: 989–94), NOS promoter (Becker et al., 1992 Plant Molecular Biology 20:

DETAILED DESCRIPTION OF THE INVENTION

Figure 5:
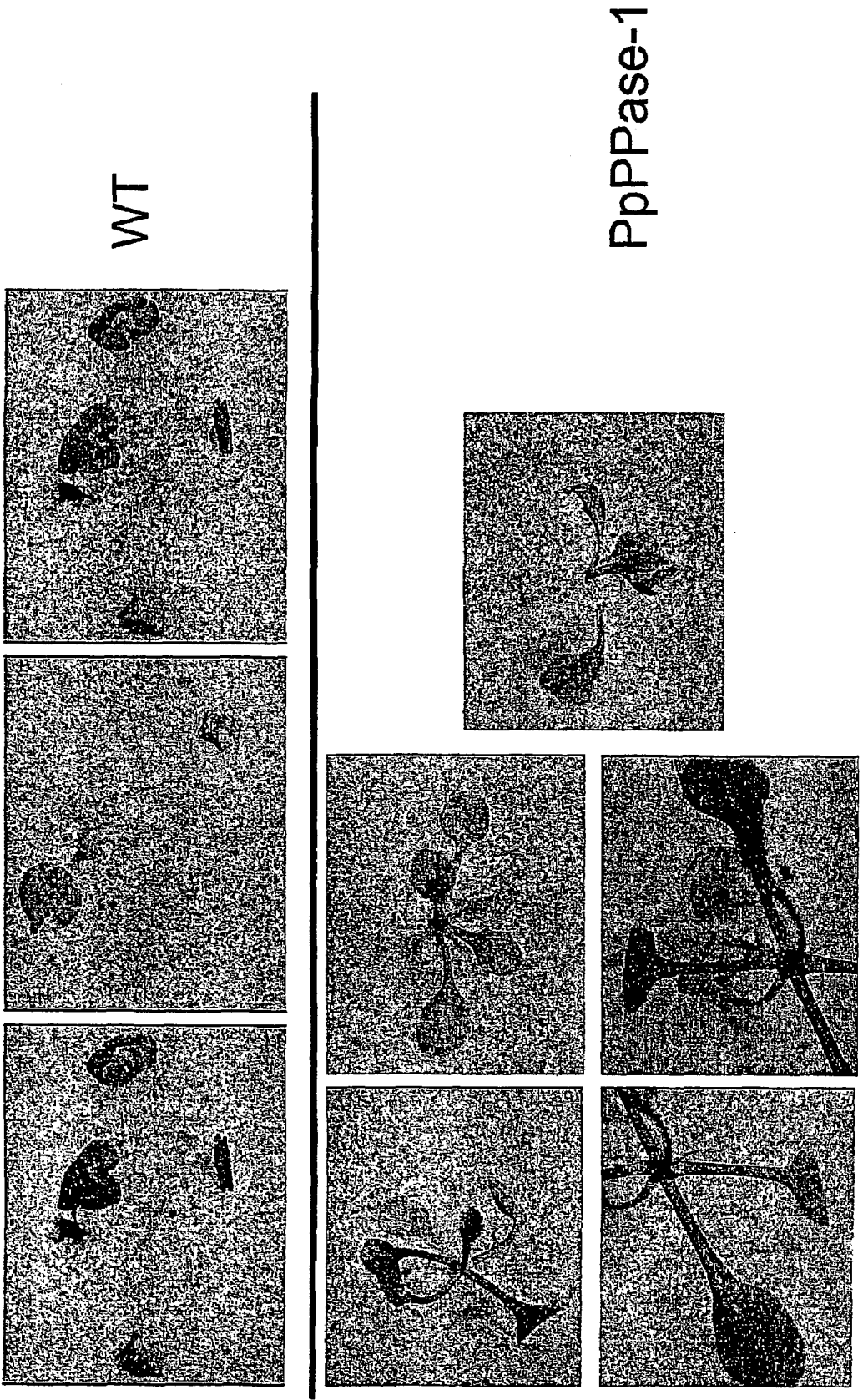
FIG. 5 shows the results of a drought stress test with PpPPase-1 transgenic and wild-type *Arabidopsis* lines. The transgenic lines display a tolerant phenotype. Individual transformant lines are shown.
Figure 6:
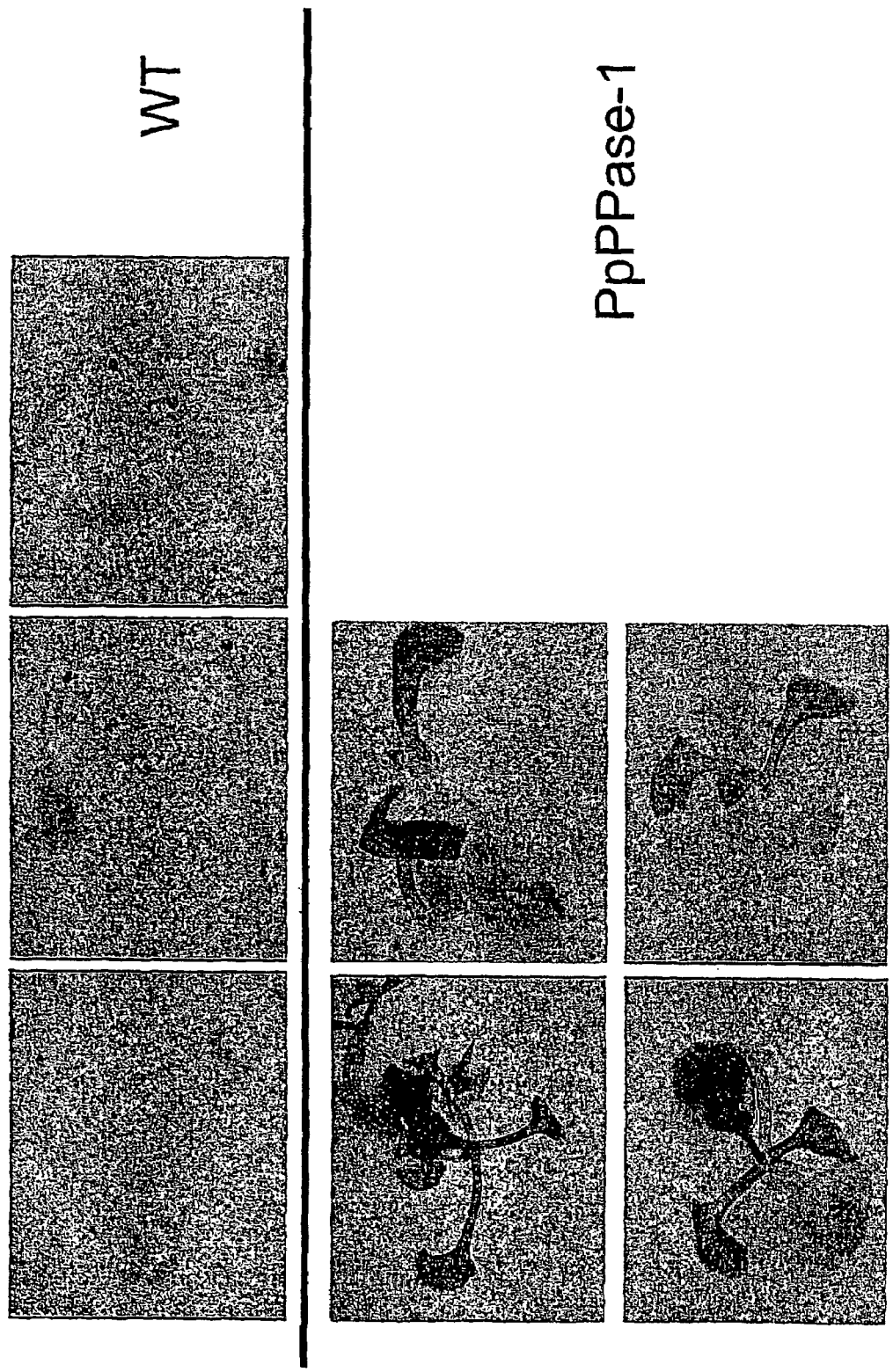
FIG. 6 shows the results of a salt stress test with PpPPase-1 transgenic and wild-type *Arabidopsis* lines. The transgenic lines display a tolerant phenotype. Individual transformant lines are shown.

The present invention may be understood more readily by reference to the following detailed description of the preferred embodiments of the invention and the Examples included herein. However, before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting. In particular, the designation of the amino acid sequences as "Pyrophoshpatase Stress-related Proteins" (PPSRPs), in no way limits the functionality of those sequences.

The present invention provides a transgenic plant transformed by a PPSRP coding nucleic acid, wherein expression of the nucleic acid sequence in the plant results in increased tolerance to environmental stress as compared to a wild type variety of the plant. The invention further provides a seed produced by a transgenic plant transformed by a PPSRP coding nucleic acid, wherein the seed contains the PPSRP coding nucleic acid, and wherein the plant is true breeding for increased tolerance to environmental stress as compared to a wild type variety of the plant. The invention further provides a seed produced by a transgenic plant expressing a PPSRP, wherein the seed contains the PPSRP, and wherein the plant is true breeding for increased tolerance to environmental stress as compared to a wild type variety of the plant. The invention further provides an agricultural product produced by any of the above-or below-described transgenic plants. As used herein, the term "variety" refers to a group of plants within a species that share constant characters that separate them from the typical form and from other possible varieties within that species. While possessing at least one distinctive trait, a variety is also characterized by some variation between individuals within the variety, based primarily on the Mendelian segregation of traits among the progeny of succeeding generations. A variety is considered "true breeding" for a particular trait if it is genetically homozygous for that trait to the extent that, when the true-breeding variety is self-pollinated, a significant amount of independent segregation of the trait among the progeny is not observed. In the present invention, the trait arises from the transgenic expression of a single DNA sequence introduced into a plant variety.

The invention further provides an isolated PPSRP. The invention provides that the PPSRP can be selected from one of the well known general classes of pyrophosphatase proteins, including those known as pyrophosphatase family I and family II (PPases). It is a novel finding of the present invention that these classes of pyrophosphatases are involved in stress tolerance in plants and that expression of a member of one of these protein classes in a plant can increase that plant's tolerance to stress. The invention further provides specific examples of PPSRP, and PPSRP coding nucleic acids, such as PPase-1. In further preferred embodiments, the PPSRP is a pyrophosphatase-1 (PPase-1) as defined in SEQ ID NO:3, and homologues thereof. Homologues of amino acid sequences are defined below.

The invention further provides an isolated PPSRP coding nucleic acid. In preferred embodiments the PPSRP coding nucleic acid is pyrophosphatase-1 (PPase-1) coding nucleic acid as defined in SEQ ID NO:2, and homologues thereof. Homologues of the nucleotide sequences are defined below. The present invention includes PPSRP coding nucleic acids that encode PPSRPs as described herein. In some embodiments, the invention provides that the PPSRP is a pyrophosphatase-1 (PPase-1) as defined in SEQ ID NO:3. In preferred embodiments the PPSRP coding nucleic acid is a pyrophosphatase-1 (PPase-1) coding nucleic acid as defined in SEQ ID NO:2. In one preferred embodiment, the nucleic acid and protein are isolated from the plant genus *Physcomitrella*. In another preferred embodiment, the nucleic acid and protein are from a *Physcomitrella patens* (*P. patens*) plant.

As used herein, the term "environmental stress" refers to any sub-optimal growing condition and includes, but is not limited to, sub-optimal conditions associated with salinity, drought, temperature, metal, chemical, pathogenic and oxidative stresses, or combinations thereof. In preferred embodiments, the environmental stress can be salinity, drought, and temperature, or combinations thereof, and in particular, can be high salinity, low water content and low temperature. It is also to be understood that as used in the specification and in the claims, "a" or "an" can mean one or more, depending upon the context in which it is used. Thus, for example, reference to "a cell" can mean that at least one cell can be utilized.

In accordance with the purposes of this invention, as embodied and broadly described herein, this invention, in one aspect, provides an isolated nucleic acid from a moss encoding a Stress-related Protein (SRP), or a portion thereof. In particular, the present invention provides nucleic acids encoding PPSRPs including the nucleic acid sequence shown in SEQ ID NO:2. The present invention also provides amino acid sequences of PPSRPs including the amino acid sequence shown in SEQ ID NO:3. As mentioned above, the present invention describes for the first time the predicted *P. patens* protein pyrophosphatase-1 (PPase-1). The present invention also describes for the first time that the *P. patens* protein pyrophosphatase-1 (PPase-1) is useful for increasing stress tolerance in plants.

A nucleic acid molecule of the present invention, e.g., a nucleic acid molecule having a nucleotide sequence of SEQ ID NO:2, or a portion thereof, can be isolated using standard molecular biology techniques and the sequence information provided herein. For example, a *P. patens* PPSRP cDNA can be isolated from a *P. patens* library using all or portion of one of the sequences of SEQ ID NO:1 as a hybridization probe and standard hybridization techniques (e.g., as described in Sambrook et al., 1989 *Molecular Cloning: A Laboratory Manual. 2nd, ed., Cold Spring Harbor Laboratory*, Cold Spring Harbor Laboratory Press, Cold Spring Harbor, N.Y.). Moreover, a nucleic acid molecule encompassing all or a portion of the sequence of SEQ ID NO:1 can be isolated by the polymerase chain reaction using oligonucleotide primers designed based upon this sequence (e.g., a nucleic acid molecule encompassing all or a portion of the sequence of SEQ ID NO:1 can be isolated by the polymerase chain reaction using oligonucleotide primers designed based upon this same sequence of SEQ ID NO:1). For example, mRNA can be isolated from plant cells (e.g., by the guanidinium-thiocyanate extraction procedure of Chirgwin et al., 1979 Biochemistry 18:5294–5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon the nucleotide sequence shown in SEQ ID NO:1. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to a PPSRP nucleotide sequence can be prepared by standard synthetic techniques, e.g., using an automated DNA synthesizer.

In a preferred embodiment, an isolated nucleic acid molecule of the invention comprises the nucleotide sequence shown in SEQ ID NO:2. The sequence of SEQ ID NO:2 corresponds to the *Physcomitrella patens* PPSRP cDNA of the invention. This cDNA comprises sequences encoding PPSRPs (i.e., the "coding region", indicated in Table 1), as well as 5' untranslated sequences and 3' untranslated sequences. It is therefore to be understood that SEQ ID NO:2 comprises both coding regions and 5' and 3' untranslated regions. Alternatively, the nucleic acid molecule can comprise only the coding region of the sequence in SEQ ID NO:2 or can contain whole genomic fragments isolated from genomic DNA. A coding region of these sequences is indicated as "ORF position".

In another preferred embodiment, an isolated nucleic acid molecule of the invention comprises a nucleic acid molecule which is a complement of the nucleotide sequence shown in SEQ ID NO:2, or a portion thereof. A nucleic acid molecule which is complementary to the nucleotide sequence shown in SEQ ID NO:2 is one which is sufficiently complementary to the nucleotide sequence shown in SEQ ID NO:2 such that it can hybridize to the nucleotide sequence shown in SEQ ID NO:2, thereby forming a stable duplex.

In still another preferred embodiment, an isolated nucleic acid molecule of the invention comprises a nucleotide sequence which is at least about 50–60%, preferably at least about 60–70%, more preferably at least about 70–80%, 80–90%, or 90–95%, and even more preferably at least about 95%, 96%, 97%, 98%, 99% or more homologous to a nucleotide sequence shown in SEQ ID NO:2, or a portion thereof. In an additional preferred embodiment, an isolated nucleic acid molecule of the invention comprises a nucleotide sequence which hybridizes, e.g., hybridizes under stringent conditions, to the nucleotide sequence shown in SEQ ID NO:2, or a portion thereof. These hybridization conditions include washing with a solution having a salt concentration of about 0.02 molar at pH 7 at about 60° C.

Moreover, the nucleic acid molecule of the invention can comprise only a portion of the coding region of the sequence in SEQ ID NO:2, for example a fragment which can be used as a probe or primer or a fragment encoding a biologically active portion of a PPSRP. The nucleotide sequences determined from the cloning of the PPSRP genes from *P. patens* allows for the generation of probes and primers designed for use in identifying and/or cloning PPSRP homologues in other cell types and organisms, as well as PPSRP homologues from other mosses or related species. Therefore this invention also provides compounds comprising the nucleic acid molecules disclosed herein, or fragments thereof. These compounds include the nucleic acid molecules attached to a moiety. These moieties include, but are not limited to, detection moieties, hybridization moieties, purification moieties, delivery moieties, reaction moieties, binding moieties, and the like. The probe/primer typically comprises substantially isolated oligonucleotide. The oligonucleotide typically comprises a region of nucleotide sequence that hybridizes under stringent conditions to at least about 12, preferably about 25, more preferably about 40, 50 or 75 consecutive nucleotides of a sense strand of the sequence set forth in SEQ ID NO:2, an anti-sense sequence of the sequence set forth in SEQ ID NO:2, or naturally occurring mutants thereof. Primers based on a nucleotide sequence of SEQ ID NO:2 can be used in PCR reactions to clone PPSRP homologues. Probes based on the PPSRP nucleotide sequences can be used to detect transcripts or genomic sequences encoding the same or homologous proteins. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express an PPSRP, such as by measuring a level of a PPSRP-encoding nucleic acid in a sample of cells, e.g., detecting PPSRP mRNA levels or determining whether a genomic PPSRP gene has been mutated or deleted.

In particular, a useful method to ascertain the level of transcription of the gene (an indicator of the amount of mRNA available for translation to the gene product) is to perform a Northern blot (for reference see, for example, Ausubel et al., 1988 Current Protocols in Molecular Biology, Wiley: N.Y.), in which a primer designed to bind to the gene of interest is labeled with a detectable tag (usually radioactive or chemiluminescent), such that when the total RNA of a culture of the organism is extracted, run on gel, transferred to a stable matrix and incubated with this probe, the binding and quantity of binding of the probe indicates the presence and also the quantity of mRNA for this gene. This information at least partially demonstrates the degree of transcription of the transformed gene. Total cellular RNA can be prepared from cells, tissues or organs by several methods, all well-known in the art, such as that described in Bormann, E. R. et al., 1992 Mol. Microbiol. 6:317–326.

To assess the presence or relative quantity of protein translated from this mRNA, standard techniques, such as a Western blot, may be employed (see, for example, Ausubel et al., 1988 Current Protocols in Molecular Biology, Wiley: N.Y.). In this process, total cellular proteins are extracted, separated by gel electrophoresis, transferred to a matrix such as nitrocellulose, and incubated with a probe, such as an antibody, which specifically binds to the desired protein. This probe is generally tagged with a chemiluminescent or calorimetric label that may be readily detected. The presence and quantity of label observed indicates the presence and quantity of the desired mutant protein present in the cell.

In one embodiment, the nucleic acid molecule of the invention encodes a protein or portion thereof which includes an amino acid sequence which is sufficiently homologous to an amino acid sequence of SEQ ID NO:3 such that the protein or portion thereof maintains the same or a similar function as the amino acid sequence to which it is compared. As used herein, the language "sufficiently homologous" refers to proteins or portions thereof which have amino acid sequences which include a minimum number of identical or equivalent (e.g., an amino acid residue which has a similar side chain as an amino acid residue in one of the ORFs of a sequence of SEQ ID NO:3) amino acid residues to a PPSRP amino acid sequence such that the protein or portion thereof is able to participate in a stress tolerance response in a plant, or more particularly can participate as a pyrophosphatase in signal transduction pathways involved in a stress tolerance response in a *Physcomitrella patens* plant Examples of such activities are also described herein. Examples of PPSRP activities are set forth in Table 1.

In another embodiment, the protein is at least about 50–60%, preferably at least about 60–70%, and more preferably at least about 70–80%, 80–90%, 90–95%, and most preferably at least about 96%, 97%, 98%, 99% or more homologous to an entire amino acid sequence shown in SEQ ID NO:3. In yet another embodiment, at least about 50–60%, preferably at least about 60–70%, and more preferably at least about 70–80%, 80–90%, 90–95%, and most preferably at least about 96%, 97%, 98%, 99% or more homologous to an entire amino acid sequence encoded by a nucleic acid sequence shown in SEQ ID NO:2.

Portions of proteins encoded by the PPSRP nucleic acid molecules of the invention are preferably biologically active portions of one of the PPSRPs. As used herein, the term "biologically active portion of a PPSRP" is intended to include a portion, e.g., a domain/motif, of a PPSRP that participates in a stress tolerance response in a plant, or more particularly participates as a pyrophosphatase in signal transduction pathways involved in a stress tolerance response in a plant, or has an activity as set forth in Table 1. To determine whether a PPSRP or a biologically active portion thereof can participate as a phosphatase in signal transduction pathways involved in a stress tolerance response in a plant, a stress analysis of a plant expressing the PPSRP may be performed. Such analysis methods are well known to those skilled in the art, as detailed in Example 7.

Additional nucleic acid fragments encoding biologically active portions of a PPSRP can be prepared by isolating a portion of one of the sequences in SEQ ID NO:3, expressing the encoded portion of the PPSRP or peptide (e.g., by recombinant expression in vitro) and assessing the activity of the encoded portion of the PPSRP or peptide.

The invention further encompasses nucleic acid molecules that differ from the nucleotide sequence shown in SEQ ID NO:2 (and portions thereof) due to degeneracy of the genetic code and thus encode the same PPSRP as that encoded by the nucleotide sequences shown in SEQ ID NO:2. In a further embodiment, the nucleic acid molecule of the invention encodes a full length *Physcomitrella patens* protein which is substantially homologous to an amino acid sequence of a polypeptide shown in SEQ ID NO:3.

In addition to the *Physcomitrella patens* PPSRP nucleotide sequence shown in SEQ ID NO:2, it will be appreciated by those skilled in the art that DNA sequence polymorphisms that lead to changes in the amino acid sequences of PPSRPs may exist within a population (e.g., the *Physcomitrella patens* population). Such genetic polymorphism in the PPSRP gene may exist among individuals within a population due to natural variation. As used herein, the terms "gene" and "recombinant gene" refer to nucleic acid molecules comprising an open reading frame encoding a PPSRP, preferably a *Physcomitrella patens* PPSRP. Such natural variations can typically result in 1–5% variance in the nucleotide sequence of the PPSRP gene. Any and all such nucleotide variations and resulting amino acid polymorphisms in a PPSRP that are the result of natural variation and that do not alter the functional activity of the PPSRPs are intended to be within the scope of the invention.

Nucleic acid molecules corresponding to natural variants and non-*Physcomitrella patens* homologues of the *Physcomitrella patens* PPSRP cDNA of the invention can be isolated based on their homology to *Physcomitrella patens* PPSRP nucleic acid disclosed herein using the *Physcomitrella patens* cDNA, or a portion thereof, as a hybridization probe according to standard hybridization techniques under stringent hybridization conditions. Accordingly, in another embodiment, an isolated nucleic acid molecule of the invention is at least 15 nucleotides in length and hybridizes under stringent conditions to the nucleic acid molecule comprising a nucleotide sequence of SEQ ID NO:2. In other embodiments, the nucleic acid is at least 30, 50, 100, 250 or more nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those skilled in the art and can be found in *Current Protocols in Molecular Biology*, 6.3.1–6.3.6, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions to a sequence of SEQ ID NO:2 corresponds to a naturally occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural *Physcomitrella patens* PPSRP.

In addition to naturally-occurring variants of the PPSRP sequence that may exist in the population, the skilled artisan will further appreciate that changes can be introduced by mutation into a nucleotide sequence of SEQ ID NO:2, thereby leading to changes in the amino acid sequence of the encoded PPSRP, without altering the functional ability of the PPSRP. For example, nucleotide substitutions leading to amino acid substitutions at "non-essential" amino acid residues can be made in a sequence of SEQ ID NO:2. A "non-essential" amino acid residue is a residue that can be altered from the wild-type sequence of the PPSRP (SEQ ID NO:3) without altering the activity of said PPSRP, whereas an "essential" amino acid residue is required for PPSRP activity. Other amino acid residues, however, (e.g., those that are not conserved or only semi-conserved in the domain having PPSRP activity) may not be essential for activity and thus are likely to be amenable to alteration without altering PPSRP activity.

Accordingly, another aspect of the invention pertains to nucleic acid molecules encoding PPSRPs that contain changes in amino acid residues that are not essential for PPSRP activity. Such PPSRPs differ in amino acid sequence from a sequence contained in SEQ ID NO:3, yet retain at least one of the PPSRP activities described herein. In one embodiment, the isolated nucleic acid molecule comprises a nucleotide sequence encoding a protein, wherein the protein comprises an amino acid sequence at least about 50% homologous to an amino acid sequence of SEQ ID NO:3 and is capable of participating in the a stress tolerance response in a plant, or more particularly participates as a pyrophosphatase in signal transduction pathways involved in a stress tolerance response in a *Physcomitrella patens* plant, or has one or more activities set forth in Table 1. Preferably, the protein encoded by the nucleic acid molecule is at least about 50–60% homologous to one of the sequences of SEQ ID NO:3, more preferably at least about 60–70% homologous to one of the sequences of SEQ ID NO:3, even more preferably at least about 70–80%, 80–90%, 90–95% homologous to the sequence of SEQ ID NO:3, and most preferably at least about 96%, 97%, 98%, or 99% homologous to the sequence of SEQ ID NO:3.

To determine the percent homology of two amino acid sequences (e.g., the sequence of SEQ ID NO:3 and a mutant form thereof) or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence (e.g., the sequence of SEQ ID NO:3) is occupied by the same amino acid residue or nucleotide as the corresponding position in the other sequence (e.g., a mutant form of the sequence selected from the polypeptide of SEQ ID NO:3), then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=numbers of identical positions/total numbers of positions×100). Preferably, the length of sequence comparison is at least 15 amino acid residues, more preferably at least 25 amino acid residues, and most preferably at least 35 amino acid residues.

Alternatively, a determination of the percent homology between two sequences can be accomplished using a mathematical algorithm. A preferred, non-limiting example of a mathematical algorithm utilized for the comparison of two sequences is the algorithm of Karlin and Altschul (1990 Proc. Natl. Acad. Sci. USA 90:5873–5877). Such an algorithm is incorporated into the NBLAST and XBLAST programs of Altschul, et al. (1990 J. Mol. Biol. 215:403–410). BLAST nucleic acid searches can be performed with the NBLAST program, score=100, wordlength=12 to obtain nucleic acid sequences homologous to PPSRP nucleic acid molecules of the invention. BLAST protein searches can be performed with the XBLAST program, score=50, wordlength=3 to obtain amino acid sequences homologous to PPSRPs of the present invention. To obtain gapped alignments for comparison purposes, Gapped BLAST can be utilized as described in Altschul et al. (1997 Nucleic Acids Res. 25:3389–3402). When utilizing BLAST and Gapped BLAST programs, the default parameters of the respective programs (e.g., XBLAST and NBLAST) can be used. Another preferred non-limiting example of a mathematical algorithm utilized for the comparison of sequences is the algorithm of Myers and Miller (CABIOS 1989). Such an algorithm is incorporated into the ALIGN program (version 2.0) that is part of the GCG sequence alignment software package. When utilizing the ALIGN program for comparing amino acid sequences, a PAM120 weight residue table, a gap length penalty of 12 and a gap penalty of 4 can be used to obtain amino acid sequences homologous to the PPSRPs of the present invention. To obtain gapped alignments for comparison purposes, Gapped BLAST can be utilized as described in Altschul et al. (1997 Nucleic Acids Res. 25:3389–3402). When utilizing BLAST and Gapped BLAST programs, the default parameters of the respective programs (e.g., XBLAST and NBLAST) can be used. Another preferred non-limiting example of a mathematical algorithm utilized for the comparison of sequences is the algorithm of Myers and Miller (CABIOS 1989). Such an algorithm is incorporated into the ALIGN program (version 2.0) that is part of the GCG sequence alignment software package. When utilizing the ALIGN program for comparing amino acid sequences, a PAM120 weight residue table, a gap length penalty of 12 and a gap penalty of 4 can be used.

An isolated nucleic acid molecule encoding a PPSRP homologous to a protein sequence of SEQ ID NO:3 can be created by introducing one or more nucleotide substitutions, additions or deletions into a nucleotide sequence of SEQ ID NO:2 such that one or more amino acid substitutions, additions or deletions are introduced into the encoded protein. Mutations can be introduced into the sequence of SEQ ID NO:2 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a PPSRP is preferably replaced with another amino acid residue from the same side chain family. Alternatively, in another embodiment, mutations can be introduced randomly along all or part of a PPSRP coding sequence, such as by saturation mutagenesis, and the resultant mutants can be screened for a PPSRP activity described herein to identify mutants that retain PPSRP activity. Following mutagenesis of the sequence of SEQ ID NO:2, the encoded protein can be expressed recombinantly and the activity of the protein can be determined by analyzing the stress tolerance of a plant expressing the protein as described in Example 7.

In addition to the nucleic acid molecules encoding PPSRPs described above, another aspect of the invention pertains to isolated nucleic acid molecules that are antisense thereto. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire PPSRP coding strand, or to only a portion thereof. In one embodiment, an antisense nucleic acid molecule is antisense to a "coding region" of the coding strand of a nucleotide sequence encoding a PPSRP. The term "coding region" refers to the region of the nucleotide sequence comprising codons which are translated into amino acid residues (e.g., the entire coding region of . . . comprises nucleotides 1 to . . . ). In another embodiment, the antisense nucleic acid molecule is antisense to a "noncoding region" of the coding strand of a nucleotide sequence encoding PPSRP. The term "noncoding region" refers to 5' and 3' sequences that flank the coding region that are not translated into amino acids (i.e., also referred to as 5' and 3' untranslated regions).

Given the coding strand sequences encoding PPSRP disclosed herein (e.g., the sequence set forth in SEQ ID NO:2), antisense nucleic acids of the invention can be designed according to the rules of Watson and Crick base pairing. The antisense nucleic acid molecule can be complementary to the entire coding region of PPSRP mRNA, but more preferably is an oligonucleotide which is antisense to only a portion of the coding or noncoding region of PPSRP mRNA. For example, the antisense oligonucleotide can be complementary to the region surrounding the translation start site of PPSRP mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a cell or generated in situ such that they hybridize with or bind to cellular mRNA and/or genomic DNA encoding a PPSRP to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic (including plant) promoters are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al., 1987 Nucleic Acids. Res. 15:6625–6641). The antisense nucleic acid molecule can also comprise a 2'-o-methylribonucleotide (Inoue et al., 1987 Nucleic Acids Res. 15:6131–6148) or a chimeric RNA-DNA analogue (Inoue et al., 1987 FEBS Lett. 215: 327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach, 1988 Nature 334:585–591)) can be used to catalytically cleave PPSRP mRNA transcripts to thereby inhibit translation of PPSRP mRNA. A ribozyme having specificity for a PPSRP-encoding nucleic acid can be designed based upon the nucleotide sequence of a PPSRP cDNA disclosed herein (i.e., SEQ ID NO:2) or on the basis of a heterologous sequence to be isolated according to methods taught in this invention. For example, a derivative of a *Tetrahymena* L-9 IVS RNA can be constructed in which the nucleotide sequence of the active site is complementary to the nucleotide sequence to be cleaved in an PPSRP-encoding mRNA. See, e.g., Cech et al. U.S. Pat. No. 4,987,071 and Cech et al. U.S. Pat. No. 5,116,742. Alternatively, PPSRP mRNA can be used to select a catalytic RNA having a specific ribonuclease activity from a pool of RNA molecules. See, e.g., Bartel, D. and Szostak, J. W., 1993 Science 261:1411–1418.

Alternatively, PPSRP gene expression can be inhibited by targeting nucleotide sequences complementary to the regulatory region of a PPSRP nucleotide sequence (e.g., a PPSRP promoter and/or enhancer) to form triple helical structures that prevent transcription of an PPSRP gene in target cells. See generally, Helene, C., 1991 Anticancer Drug Des. 6(6): 569–84; Helene, C. et al., 1992 Ann. N.Y. Acad. Sci 660: 27–36; and Maher, L. J., 1992 Bioassays 14(12):807–15.

The invention further provides an isolated recombinant expression vector comprising a nucleic acid as described above, wherein expression of the vector in a host cell results in increased tolerance to environmental stress as compared to a wild type variety of the host cell. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990) or see: Gruber and Crosby, in: Methods in Plant Molecular Biology and Biotechnology, eds. Glick and Thompson, Chapter 7, 89–108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., PPSRPs, mutant forms of PPSRPs, fusion proteins, etc.).

The recombinant expression vectors of the invention can be designed for expression of PPSRPs in prokaryotic or eukaryotic cells. For example, PPSRP genes can be expressed in bacterial cells such as *C. glutamicum*, insect cells (using baculovirus expression vectors), yeast and other fungal cells (see Romanos, M. A. et al., 1992 Foreign gene expression in yeast: a review, Yeast 8:423–488; van den Hondel, C. A. M. J. J. et al., 1991 Heterologous gene expression in filamentous fingi, in: More Gene Manipulations in Fungi, J. W. Bennet & L. L. Lasure, eds., p. 396–428: Academic Press: San Diego; and van den Hondel, C. A. M. J. J. & Punt, P. J., 1991 Gene transfer systems and vector development for filamentous fungi, in: Applied Molecular Genetics of Fungi Peberdy, J. F. et al., eds., p. 1–28, Cambridge University Press: Cambridge), algae (Falciatore et al., 1999 Marine Biotechnology 1(3):239–251), ciliates of the types: Holotrichia, Peritrichia, Spirotrichia, Suctoria, *Tetrahymena, Paramecium, Colpidium*, Glaucoma, Platyophrya, Potomacus, Pseudocohnilembus, *Euplotes*, Engelmaniella, and *Stylonychia*, especially of the genus *Stylonychia lemnae* with vectors following a transformation method as described in WO 98/01572 and multicellular plant cells (see Schmidt, R. and Willmitzer, L., 1988 High efficiency *Agrobacterium tumefaciens*-mediated transformation of *Arabidopsis thaliana* leaf and cotyledon explants, Plant Cell Rep. 583–586); Plant Molecular Biology and Biotechnology, C Press, Boca Raton, Fla., chapter 6/7, S. 71–119 (1993); F. F. White, B. Jenes et al., Techniques for Gene Transfer, in: Transgenic Plants, Vol. 1, Engineering and Utilization, eds. Kung und R. Wu, 128–43, Academic Press: 1993; Potrykus, 1991 Annu. Rev. Plant Physiol. Plant Molec. Biol. 42:205–225 and references cited therein) or mammalian cells. Suitable host cells are discussed further in Goeddel, *Gene Expression Technology: Methods in Enzymology* 185, Academic Press: San Diego, Calif. (1990). Alternatively, the recombinant expression vector can be transcribed and translated in vitro, for example using T7 promoter regulatory sequences and T7 polymerase.

Expression of proteins in prokaryotes is most often carried out with vectors containing constitutive or inducible promoters directing the expression of either fusion or non-fusion proteins. Fusion vectors add a number of amino acids to a protein encoded therein, usually to the amino terminus of the recombinant protein but also to the C-terminus or fused within suitable regions in the proteins. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Typical fusion expression vectors include pGEX (Pharmacia Biotech Inc; Smith, D. B. and Johnson, K. S., 1988 Gene 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the PPSRP is cloned into a pGEX expression vector to create a vector encoding a fusion protein comprising, from the N-terminus to the C-terminus, GST-thrombin cleavage site-X protein. The fusion protein can be purified by affinity chromatography using glutathione-agarose resin. Recombinant PPSRP unfused to GST can be recovered by cleavage of the fusion protein with thrombin.

Examples of suitable inducible non-fusion *E. coli* expression vectors include pTrc (Amann et al., 1988 Gene 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant protein expression is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in the bacterium chosen for expression, such as *C. glutamicum* (Wada et al., 1992 Nucleic Acids Res. 20:2111–2118). Such alteration of nucleic acid sequences of the invention can be carried out by standard DNA synthesis techniques.

In another embodiment, the PPSRP expression vector is a yeast expression vector. Examples of vectors for expression in yeast *S. cerevisiae* include pYepSec1 (Baldari, et al., 1987 Embo J. 6:229–234), pMFa (Kurjan and Herskowitz, 1982 Cell 30:933–943), pJRY88 (Schultz et al., 1987 Gene 54:113–123), and pYES2 (Invitrogen Corporation, San Diego, Calif.). Vectors and methods for the construction of vectors appropriate for use in other fungi, such as the filamentous fungi, include those detailed in: van den Hondel, C. A. M. J. J. & Punt, P. J. (1991) "Gene transfer systems and vector development for filamentous fungi, in: Applied Molecular Genetics of Fungi, J. F. Peberdy, et al., eds., p. 1–28, Cambridge University Press: Cambridge.

Alternatively, the PPSRPs of the invention can be expressed in insect cells using baculovirus expression vectors. Baculovirus vectors available for expression of proteins in cultured insect cells (e.g., Sf 9 cells) include the pAc series (Smith et al., 1983 Mol. Cell Biol. 3:2156–2165) and the pVL series (Lucklow and Summers, 1989 Virology 170:31–39).

In yet another embodiment, a nucleic acid of the invention is expressed in mammalian cells using a mammalian expression vector. Examples of mammalian expression vectors include pCDM8 (Seed, B., 1987 Nature 329:840) and pMT2PC (Kaufman et al., 1987 EMBO J. 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed, Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987 Genes Dev. 1:268–277), lymphoid-specific promoters (Calame and Eaton, 1988 Adv. Immunol. 43:235–275), in particular promoters of T cell receptors (Winoto and Baltimore, 1989 EMBO J. 8:729–733) and immunoglobulins (Banerji et al., 1983 Cell 33:729–740; Queen and Baltimore, 1983 Cell 33:741–748), neuron-specific promoters (e.g., the neurofilament promoter; Byrne and Ruddle, 1989 *PNAS* 86:5473–5477), pancreas-specific promoters (Edlund et al., 1985 Science 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990 Science 249:374–379) and the fetoprotein promoter (Campes and Tilghman, 1989 Genes Dev. 3:537–546).

In another embodiment, the PPSRPs of the invention may be expressed in unicellular plant cells (such as algae) (see Falciatore et al., 1999 Marine Biotechnology 1(3):239–251 and references therein) and plant cells from higher plants (e.g., the spermatophytes, such as crop plants). Examples of plant expression vectors include those detailed in: Becker, D., Kemper, E., Schell, J. and Masterson, R., 1992 New plant binary vectors with selectable markers located proximal to the left border, *Plant Mol. Biol.* 20: 1195–1197; and Bevan, M. W., 1984 Binary *Agrobacterium* vectors for plant transformation, Nucl. Acid. Res. 12:8711–8721; Vectors for Gene Transfer in Higher Plants; in: Transgenic Plants, Vol. 1, Engineering and Utilization, eds.: Kung and R. Wu, Academic Press, 1993, S. 15–38.

A plant expression cassette preferably contains regulatory sequences capable of driving gene expression in plants cells and which are operably linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984 EMBO J. 3:835) or functional equivalents thereof but also all other terminators functionally active in plants are suitable.

As plant gene expression is very often not limited on transcriptional levels, a plant expression cassette preferably contains other operably linked sequences like translational enhancers such as the overdrive-sequence containing the 5'-untranslated leader sequence from tobacco mosaic virus enhancing the protein per RNA ratio (Gallie et al., 1987 Nucl. Acids Research 15:8693–8711).

Plant gene expression has to be operably linked to an appropriate promoter conferring gene expression in a timely, cell or tissue specific manner. Preferred are promoters driving constitutive expression (Benfey et al., 1989 EMBO J. 8:2195–2202) like those derived from plant viruses like the 35S CAMV (Franck et al., 1980 Cell 21:285–294), the 19S CaMV (see also U.S. Pat. No. 5,352,605 and WO8402913) or plant promoters like those from Rubisco small subunit described in U.S. Pat. No. 4,962,028.

Other preferred sequences for use in plant gene expression cassettes are targeting-sequences necessary to direct the gene product in its appropriate cell compartment (for review see Kermode, 1996 Crit. Rev. Plant Sci. 15(4):285–423 and references cited therein) such as the vacuole, the nucleus, all types of plastids like amyloplasts, chloroplasts, chromoplasts, the extracellular space, mitochondria, the endoplasmic reticulum, oil bodies, peroxisomes and other compartments of plant cells. Plant gene expression can also be facilitated via an inducible promoter (for review see Gatz, 1997 Annu. Rev. Plant Physiol. Plant Mol. Biol. 48:89–108). Chemically inducible promoters are especially suitable if gene expression is wanted to occur in a time specific manner. Examples of such promoters are a salicylic acid inducible promoter (WO 95/19443), a tetracycline inducible promoter (Gatz et al., 1992 Plant J. 2:397–404) and an ethanol inducible promoter (WO 93/21334).

Also, suitable promoters responding to biotic or abiotic stress conditions are those such as the pathogen inducible PRP1-gene promoter (Ward et al., 1993 Plant. Mol. Biol. 22:361–366), the heat inducible hsp80-promoter from tomato (U.S. Pat. No. 5,187,267), cold inducible alpha-amylase promoter from potato (WO 96/12814) or the wound-inducible pinII-promoter (EP 375091). For other examples of drought, cold, and salt-inducible promoters, such as the RD29A promoter, see Yamaguchi-Shinozalei et al. (1993 Mol. Gen. Genet. 236:331–340).

Especially those promoters are preferred which confer gene expression in specific tissues and organs, such as guard cells and the root hair cells. Suitable promoters include the napin-gene promoter from rapeseed (U.S. Pat. No. 5,608, 152), the USP-promoter from *Vicia faba* (Baeumlein et al., 1991 Mol Gen Genet. 225(3):459–67), the oleosin-promoter from *Arabidopsis* (WO9845461), the phaseolin-promoter from *Phaseolus vulgaris* (U.S. Pat. No. 5,504,200), the Bce4-promoter from Brassica (WO9113980) or the legumin B4 promoter (LeB4; Baeumlein et al., 1992 Plant Journal, 2(2):233–9) as well as promoters conferring seed specific expression in monocot plants like maize, barley, wheat, rye, rice, etc. Suitable promoters to note are the lpt2 or lpt1-gene promoter from barley (WO 95/15389 and WO 95/23230) or those described in WO 99/16890 (promoters from the barley hordein-gene, rice glutelin gene, rice oryzin gene, rice prolamin gene, wheat gliadin gene, wheat glutelin gene, maize zein gene, oat glutelin gene, Sorghum kasirin-gene and rye secalin gene).

Also especially suited are promoters that confer plastid-specific gene expression as plastids are the compartment where precursors and some end products of lipid biosynthesis are synthesized. Suitable promoters are the viral RNA-polymerase promoter described in WO 95/16783 and WO 97/06250 and the clpP-promoter from *Arabidopsis* described in WO 99/46394.

The invention further provides a recombinant expression vector comprising a DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to PPSRP mRNA. Regulatory sequences operatively linked to a nucleic acid molecule cloned in the antisense orientation can be chosen which direct the continuous expression of the antisense RNA molecule in a variety of cell types. For instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986 and Mol et al., 1990 FEBS Letters 268:427–430.

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a PPSRP can be expressed in bacterial cells such as *C. glutamicum*, insect cells, fungal cells or mammalian cells (such as Chinese hamster ovary cells (CHO) or COS cells), algae, ciliates, plant cells, fungi or other microorganisms like *C. glutamicum*. Other suitable host cells are known to those skilled in the art.

Vector DNA can be introduced into prokaryotic or eukaryotic cells via conventional transformation or transfection techniques. As used herein, the terms "transformation", "transfection", "conjugation" and "transduction" are intended to refer to a variety of art-recognized techniques for introducing foreign nucleic acid (e.g., DNA) into a host cell, including calcium phosphate or calcium chloride co precipitation, DEAE-dextran-mediated transfection, lipofection, natural competence, chemical-mediated transfer and electroporation. Suitable methods for transforming or transfecting host cells including plant cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989) and other laboratory manuals such as Methods in Molecular Biology, 1995, Vol. 44, Agrobacterium protocols, ed: Gartland and Davey, Humana Press, Totowa, N.J. As biotic and abiotic stress tolerance is a general trait wished to be inherited into a wide variety of plants like maize, wheat, rye, oat, triticale, rice, barley, soybean, peanut, cotton, rapeseed and canola, manihot, pepper, sunflower and tagetes, solanaceous plants like potato, tobacco, eggplant, and tomato, Vicia species, pea, alfalfa, bushy plants (coffee, cacao, tea), Salix species, trees (oil palm, coconut), perennial grasses and forage crops, these crops plants are also preferred target plants for a genetic engineering as one further embodiment of the present invention.

In particular, the invention provides a method of producing a transgenic plant with a PPSRP coding nucleic acid, wherein expression of the nucleic acid in the plant results in increased tolerance to environmental stress as compared to a wild type variety of the plant comprising: (a) transforming a plant cell with an expression vector comprising a PPSRP nucleic acid, and (b) generating from the plant cell a transgenic plant with a increased tolerance to environmental stress as compared to a wild type variety of the plant. In preferred embodiments, the PPSRP is as described above. In preferred embodiments, the PPSRP coding nucleic acid is as described above. The invention also provides a method of increasing expression of a gene of interest within a host cell as compared to a wild type variety of the host cell, wherein the gene of interest is transcribed in response to a PPSRP, comprising: (a) transforming the host cell with an expression vector comprising a PPSRP coding nucleic acid, and (b) expressing the PPSRP within the host cell, thereby increasing the expression of the gene transcribed in response to the PPSRP as compared to a wild type variety of the host cell. In preferred embodiments, the PPSRP is as described above. In preferred embodiments, the PPSRP coding nucleic acid is as described above.

For such plant transformation, binary vectors such as pBinAR can be used (Höfgen and Willmitzer, 1990 Plant Science 66:221–230). Construction of the binary vectors can be performed by ligation of the cDNA in sense or antisense orientation into the T-DNA. 5-prime to the cDNA a plant promoter activates transcription of the cDNA. A polyadenylation sequence is located 3-prime to the cDNA. Tissue-specific expression can be archived by using a tissue specific promoter. For example, seed-specific expression can be archived by cloning the napin or LeB4 or USP promoter 5-prime to the cDNA. Also, any other seed specific promoter element can be used. For constitutive expression within the whole plant, the CaMV 35S promoter can be used. The expressed protein can be targeted to a cellular compartment using a signal peptide, for example for plasmids, mitochondria or endoplasmic reticulum (Kermode, Crit. Rev. Plant Sci., 1996 4 (15):285–423). The signal peptide is cloned 5-prime in frame to the cDNA to archive subcellular localization of the fusion protein.

*Agrobacterium* mediated plant transformation can be performed using for example the GV3101(p90) (Koncz and Schell, 1986 Mol. Gen. Genet. 204:383–396) or LBA4404 (Clontech) *Agrobacterium tumefaciens* strain. Transformation can be performed by standard transformation techniques (Deblaere et al., 1994 Nucl. Acids. Res. 13:4777–4788). In one embodiment, promoters that are responsive to abiotic stresses can be used with, such as the *Arabidopsis* promoter RD29A, the nucleic acid sequences disclosed herein. One skilled in the art will recognize that the promoter used should be operatively linked to the nucleic acid such that the promoter causes transcription of the nucleic acid which results in the synthesis of a mRNA which encodes a polypeptide. Alternatively, the RNA can be an antisense RNA for use in affecting subsequent expression of the same or another gene or genes.

*Agrobacterium* mediated plant transformation can be performed using standard transformation and regeneration techniques (Gelvin, Stanton B. and Schilperoort, Robert A, Plant Molecular Biology Manual, 2nd Ed.—Dordrecht: Kluwer Academic Publ., 1995.—in Sect., Ringbuc Zentrale Signatur: BT11-P ISBN 0-7923-2731-4; Glick, Bernard R.; Thompson, John E., Methods in Plant Molecular Biology and Biotechnology, Boca Raton: CRC Press, 1993.—360 S,ISBN 0-8493-5164-2). For example, rapeseed can be transformed via cotyledon or hypocotyl transformation (Moloney et al., 1989 Plant cell Report 8:238–242; De Block et al., 1989 Plant Physiol. 91:694–701). Use of antibiotica for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., 1994 Plant Cell Report 13: 282–285. Additionally, transformation of soybean can be performed using for example a technique described in EP=0424 047, U.S. Pat. No. 5,322,783 (Pioneer Hi-Bred International) or in EP 0397 687, U.S. Pat. No. 5,376,543, U.S. Pat. No. 5,169,770 (University Toledo).

Plant transformation using particle bombardment, Polyethylene Glycol mediated DNA uptake or via the Silicon Carbide Fiber technique is for example described by Freeling and Walbot "The maize handbook" Springer Verlag: New York (1993) ISBN 3-540-97826-7. A specific example of maize transformation is found in U.S. Pat. No. 5,990,387 and a specific example of wheat transformation can be found in WO 93/07256.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate or in plants that confer resistance towards a herbicide such as glyphosate or glufosinate. Nucleic acid molecules encoding a selectable marker can be introduced into a host cell on the same vector as that encoding an PPSRP or can be introduced on a separate vector. Cells stably transfected with the introduced nucleic acid molecule can be identified by, for example, drug selection (e.g., cells that have incorporated the selectable marker gene will survive, while the other cells die).

To create a homologous recombinant microorganism, a vector is prepared which contains at least a portion of a PPSRP gene into which a deletion, addition or substitution has been introduced to thereby alter, e.g., functionally disrupt, the PPSRP gene. Preferably, this PPSRP gene is a *Physcomitrella patens* PPSRP gene, but it can be a homologue from a related plant or even from a mammalian, yeast, or insect source. In a preferred embodiment, the vector is designed such that, upon homologous recombination, the endogenous PPSRP gene is functionally disrupted (i.e., no longer encodes a functional protein; also referred to as a knock-out vector). Alternatively, the vector can be designed such that, upon homologous recombination, the endogenous PPSRP gene is mutated or otherwise altered but still encodes functional protein (e.g., the upstream regulatory region can be altered to thereby alter the expression of the endogenous PPSRP). To create a point mutation via homologous recombination, DNA-RNA hybrids can be used in a technique known as chimeraplasty (Cole-Strauss et al., 1999 Nucleic Acids Research 27(5):1323–1330 and Kmiec, 1999 Gene therapy American Scientist. 87(3):240–247). Homologous recombination procedures in *Physcomitrella patens* are also well known in the art and are contemplated for use herein.

Whereas in the homologous recombination vector, the altered portion of the PPSRP gene is flanked at its 5' and 3' ends by additional nucleic acid molecule of the PPSRP gene to allow for homologous recombination to occur between the exogenous PPSRP gene carried by the vector and an endogenous PPSRP gene in a microorganism or plant. The additional flanking PPSRP nucleic acid molecule is of sufficient length for successful homologous recombination with the endogenous gene. Typically, several hundreds of base pairs up to kilobases of flanking DNA (both at the 5' and 3' ends) are included in the vector (see e.g., Thomas, K. R., and Capeechi, M. R., 1987 Cell 51:503 for a description of homologous recombination vectors or Strepp et al., 1998 PNAS, 95 (8):4368–4373 for cDNA based recombination in *Physcomitrella patens*). The vector is introduced into a microorganism or plant cell (e.g., via polyethylene glycol mediated DNA) and cells in which the introduced PPSRP gene has homologously recombined with the endogenous PPSRP gene are selected, using art-known techniques.

In another embodiment, recombinant microorganisms can be produced which contain selected systems which allow for regulated expression of the introduced gene. For example, inclusion of a PPSRP gene on a vector placing it under control of the lac operon permits expression of the PPSRP gene only in the presence of IPTG. Such regulatory systems are well known in the art.

A host cell of the invention, such as a prokaryotic or eukaryotic host cell in culture, can be used to produce (i.e., express) a PPSRP. An alternate method can be applied in addition in plants by the direct transfer of DNA into developing flowers via electroporation or Agrobacterium medium gene transfer. Accordingly, the invention further provides methods for producing PPSRPs using the host cells of the invention. In one embodiment, the method comprises culturing the host cell of invention (into which a recombinant expression vector encoding a PPSRP has been introduced, or into which genome has been introduced a gene encoding a wild-type or altered PPSRP) in a suitable medium until PPSRP is produced. In another embodiment, the method further comprises isolating PPSRPs from the medium or the host cell.

Another aspect of the invention pertains to isolated PPSRPs, and biologically active portions thereof. An "isolated" or "purified" protein or biologically active portion thereof is free of some of the cellular material when produced by recombinant DNA techniques, or chemical precursors or other chemicals when chemically synthesized. The language "substantially free of cellular material" includes preparations of PPSRP in which the protein is separated from some of the cellular components of the cells in which it is naturally or recombinantly produced. In one embodiment, the language "substantially free of cellular material" includes preparations of PPSRP having less than about 30% (by dry weight) of non-PPSRP (also referred to herein as a "contaminating protein"), more preferably less than about 20% of non-PPSRP, still more preferably less than about 10% of non-PPSRP, and most preferably less than about 5% non-PPSRP. When the PPSRP or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of PPSRP in which the protein is separated from chemical precursors or other chemicals that are involved in the synthesis of the protein. In one embodiment, the language "substantially free of chemical precursors or other chemicals" includes preparations of PPSRP having less than about 30% (by dry weight) of chemical precursors or non-PPSRP chemicals, more preferably less than about 20% chemical precursors or non-PPSRP chemicals, still more preferably less than about 10% chemical precursors or non-PPSRP chemicals, and most preferably less than about 5% chemical precursors or non-PPSRP chemicals. In preferred embodiments, isolated proteins or biologically active portions thereof lack contaminating proteins from the same organism from which the PPSRP is derived. Typically, such proteins are produced by recombinant expression of, for example, a *Physcomitrella patens* PPSRP in plants other than *Physcomitrella patens* or microorganisms such as *C. glutamicum*, ciliates, algae or fungi.

An isolated PPSRP or a portion thereof of the invention can participate in a stress tolerance response in a plant, or more particularly can participate as a pyrophosphatase in signal transduction pathways involved in a stress tolerance response in a *Physcomitrella patens* plant, or has one or more of the activities set forth in Table 1. In preferred embodiments, the protein or portion thereof comprises an amino acid sequence which is sufficiently homologous to an amino acid sequence encoded by a nucleic acid of SEQ ID NO:2 such that the protein or portion thereof maintains the ability to participate in the metabolism of compounds necessary for the construction of cellular membranes in *Physcomitrella patens*, or in the transport of molecules across these membranes. The portion of the protein is preferably a biologically active portion as described herein. In another preferred embodiment, a PPSRP of the invention has an amino acid sequence of SEQ ID NO:3. In yet another preferred embodiment, the PPSRP has an amino acid sequence which is encoded by a nucleotide sequence which hybridizes, e.g., hybridizes under stringent conditions, to a nucleotide sequence of SEQ ID NO:2. In still another preferred embodiment, the PPSRP has an amino acid sequence which is at least about 50–60%, preferably at least about 60–70%, more preferably at least about 70–80%, 80–90%, 90–95%, and even more preferably at least about 96%, 97%, 98%, 99% or more homologous to the amino acid sequence of SEQ ID NO:3. The preferred PPSRPs of the present invention also preferably possess at least one of the PPSRP activities described herein. For example, a preferred PPSRP of the present invention includes an amino acid sequence encoded by a nucleotide sequence which hybridizes, e.g., hybridizes under stringent conditions, to a nucleotide sequence of SEQ ID NO:2, and which can participate can participate in a stress tolerance response in a plant, or more particularly can participate as a pyrophosphatase in signal transduction pathways involved in a stress tolerance response in a *Physcomitrella patens* plant, or which has one or more of the activities set forth in Table 1.

In other embodiments, the PPSRP is substantially homologous to an amino acid sequence of SEQ ID NO:3 and retains the functional activity of the protein of SEQ ID NO:3, yet differs in amino acid sequence due to natural variation or mutagenesis, as described in detail above. Accordingly, in another embodiment, the PPSRP is a protein which comprises an amino acid sequence which is at least about 50–60%, preferably at least about 60–70%, and more preferably at least about 70–80, 80–90, 90–95%, and most preferably at least about 96%, 97%, 98%, 99% or more homologous to an entire amino acid sequence of SEQ ID NO:3 and which has at least one of the PPSRP activities described herein. In another embodiment, the invention pertains to a full *Physcomitrella patens* protein which is substantially homologous to an entire amino acid sequence encoded by a nucleic acid of SEQ ID NO:2.

Biologically active portions of an PPSRP include peptides comprising amino acid sequences derived from the amino acid sequence of an PPSRP, e.g., an amino acid sequence of SEQ ID NO:3 or the amino acid sequence of a protein homologous to a PPSRP, which include fewer amino acids than a full length PPSRP or the full length protein which is homologous to an PPSRP, and exhibit at least one activity of an PPSRP. Typically, biologically active portions (peptides, e.g., peptides which are, for example, 5, 10, 15, 20, 30, 35, 36, 37, 38, 39, 40, 50, 100 or more amino acids in length) comprise a domain or motif with at least one activity of a PPSRP. Moreover, other biologically active portions, in which other regions of the protein are deleted, can be prepared by recombinant techniques and evaluated for one or more of the activities described herein. Preferably, the biologically active portions of a PPSRP include one or more selected domains/motifs or portions thereof having biological activity.

PPSRPs are preferably produced by recombinant DNA techniques. For example, a nucleic acid molecule encoding the protein is cloned into an expression vector (as described above), the expression vector is introduced into a host cell (as described above) and the PPSRP is expressed in the host cell. The PPSRP can then be isolated from the cells by an appropriate purification scheme using standard protein purification techniques. Alternative to recombinant expression, a PPSRP, polypeptide, or peptide can be synthesized chemically using standard peptide synthesis techniques. Moreover, native PPSRP can be isolated from cells (e.g., *Physcomitrella patens*), for example using an anti-PPSRP antibody, which can be produced by standard techniques utilizing a PPSRP or fragment thereof of this invention.

The invention also provides PPSRP chimeric or fusion proteins. As used herein, a PPSRP "chimeric protein" or "fusion protein" comprises a PPSRP polypeptide operatively linked to a non-PPSRP polypeptide. An "PPSRP polypeptide" refers to a polypeptide having an amino acid sequence corresponding to a PPSRP, whereas a "non-PPSRP polypeptide" refers to a polypeptide having an amino acid sequence corresponding to a protein which is not substantially homologous to the PPSRP, e.g., a protein which is different from the PPSRP and which is derived from the same or a different organism. Within the fusion protein, the term "operatively linked" is intended to indicate that the PPSRP polypeptide and the non-PPSRP polypeptide are fused to each other so that both sequences fulfill the proposed function attributed to the sequence used. The non-PPSRP polypeptide can be fused to the N-terminus or C-terminus of the PPSRP polypeptide. For example, in one embodiment, the fusion protein is a GST-PPSRP fusion protein in which the PPSRP sequences are fused to the C-terminus of the GST sequences. Such fusion proteins can facilitate the purification of recombinant PPSRPs. In another embodiment, the fission protein is a PPSRP containing a heterologous signal sequence at its N-terminus. In certain host cells (e.g., mammalian host cells), expression and/or secretion of a PPSRP can be increased through use of a heterologous signal sequence.

Preferably, a PPSRP chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, for example, *Current Protocols in Molecular Biology*, Eds. Ausubel et al. John Wiley & Sons: 1992). Moreover, many expression vectors are commercially available that already encode a fusion moiety (e.g., a GST polypeptide). A PPSRP-encoding nucleic acid can be cloned into such an expression vector such that the fusion moiety is linked in-frame to the PPSRP.

Homologues of the PPSRP can be generated by mutagenesis, e.g., discrete point mutation or truncation of the PPSRP. As used herein, the term "homologue" refers to a variant form of the PPSRP which acts as an agonist or antagonist of the activity of the PPSRP. An agonist of the PPSRP can retain substantially the same, or a subset, of the biological activities of the PPSRP. An antagonist of the PPSRP can inhibit one or more of the activities of the naturally occurring form of the PPSRP, by, for example, competitively binding to a downstream or upstream member of the cell membrane component metabolic cascade which includes the PPSRP, or by binding to an PPSRP which mediates transport of compounds across such membranes, thereby preventing translocation from taking place.

In an alternative embodiment, homologues of the PPSRP can be identified by screening combinatorial libraries of mutants, e.g., truncation mutants, of the PPSRP for PPSRP agonist or antagonist activity. In one embodiment, a variegated library of PPSRP variants is generated by combinatorial mutagenesis at the nucleic acid level and is encoded by a variegated gene library. A variegated library of PPSRP variants can be produced by, for example, enzymatically ligating a mixture of synthetic oligonucleotides into gene sequences such that a degenerate set of potential PPSRP sequences is expressible as individual polypeptides, or alternatively, as a set of larger fusion proteins (e.g., for phage display) containing the set of PPSRP sequences therein. There are a variety of methods which can be used to produce libraries of potential PPSRP homologues from a degenerate oligonucleotide sequence. Chemical synthesis of a degenerate gene sequence can be performed in an automatic DNA synthesizer, and the synthetic gene is then ligated into an appropriate expression vector. Use of a degenerate set of genes allows for the provisions in one mixture, of all of the sequences encoding the desired set of potential PPSRP sequences. Methods for synthesizing degenerate oligonucleotides are known in the art (see, e.g., Narang, S. A., 1983 Tetrahedron 39:3; Itakura et al., 1984 Annu. Rev. Biochem. 53:323; Itakura et al., 1984 Science 198:1056; Ike et al., 1983 Nucleic Acid Res. 11:477.

In addition, libraries of fragments of the PPSRP coding can be used to generate a variegated population of PPSRP fragments for screening and subsequent selection of homologues of a PPSRP. In one embodiment, a library of coding sequence fragments can be generated by treating a double stranded PCR fragment of a PPSRP coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the PPSRP.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of PPSRP homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of fictional mutants in the libraries, can be used in combination with the screening assays to identify PPSRP homologues (Arkin and Yourvan, 1992 PNAS 89:7811–7815; Delgrave et al., 1993 Protein Engineering 6(3):327–331). In another embodiment, cell based assays can be exploited to analyze a variegated PPSRP library, using methods well known in the art. The present invention further provides a method of identifying a novel PPSRP, comprising (a) raising a specific antibody response to a PPSRP, or fragment thereof, as described above; (b) screening putative PPSRP material with the antibody, wherein specific binding of the antibody to the material indicates the presence of a potentially novel PPSRP; and (c) analyzing the bound material in comparison to known PPSRP to determine its novelty.

The nucleic acid molecules, proteins, protein homologues, fusion proteins, primers, vectors, and host cells described herein can be used in one or more of the following methods: identification of *Physcomitrella patens* and related organisms; mapping of genomes of organisms related to *Physcomitrella patens*; identification and localization of *Physcomitrella patens* sequences of interest; evolutionary studies; determination of PPSRP regions required for function; modulation of an PPSRP activity; modulation of the metabolism of one or more cell functions; modulation of the transmembrane transport of one or more compounds; and modulation of stress resistance.

The moss *Physcomitrella patens* represents one member of the mosses. It is related to other mosses such as *Ceratodon purpureus* which is capable of growth in the absence of light. Mosses like *Ceratodon* and *Physcomitrella* share a high degree of homology on the DNA sequence and polypeptide level allowing the use of heterologous screening of DNA molecules with probes evolving from other mosses or organisms, thus enabling the derivation of a consensus sequence suitable for heterologous screening or functional annotation and prediction of gene functions in third species. The ability to identify such functions can therefore have significant relevance, e.g., prediction of substrate specificity of enzymes. Further, these nucleic acid molecules may serve as reference points for the mapping of moss genomes, or of genomes of related organisms.

The PPSRP nucleic acid molecules of the invention have a variety of uses. Most importantly, the nucleic acid and amino acid sequences of the present invention can be used to transform plants, thereby inducing tolerance to stresses such as drought, high salinity and cold. The present invention therefore provides a transgenic plant transformed by a PPSRP coding nucleic acid, wherein expression of the nucleic acid sequence in the plant results in increased tolerance to environmental stress as compared to a wild type variety of the plant. The transgenic plant can be a monocot or a dicot. The invention further provides that the transgenic plant can be selected from maize, wheat, rye, oat, triticale, rice, barley, soybean, peanut, cotton, rapeseed, canola, manihot, pepper, sunflower, tagetes, solanaceous plants, potato, tobacco, eggplant, tomato, Vicia species, pea, alfalfa, coffee, cacao, tea, Salix species, oil palm, coconut, perennial grass and forage crops, for example. In particular, the present invention describes using the expression of Ppase-1 (SEQ ID NO:3) to engineer drought-tolerant plants. This strategy has herein been demonstrated for *Arabidopsis thaliana*, Rapeseed/Canola, soybeans, corn and wheat but its application is not restricted to these plants. Accordingly, the invention provides a transgenic plant containing a PPSRP, such as Ppase-1 as defined above, including homologues, wherein the environmental stress is drought. This invention also describes the principle of using over-expression of Ppase-1 (SEQ ID NO:3) to engineer salt-tolerant plants. Again, this strategy has herein been demonstrated for *Arabidopsis thaliana*, Rapeseed/Canola, soybeans, corn and wheat but its application is not restricted to these plants. Accordingly, the invention provides a transgenic plant containing the PPSRP such as Ppase-1 as defined above, including homologues, wherein the environmental stress is salinity.

The present invention also provides methods of modifying stress tolerance of a plant comprising, modifying the expression of a PPSRP in the plant. The invention provides that this method can be performed such that the stress tolerance is either increased or decreased.

Furthermore, this method can be used wherein the plant is either transgenic or not transgenic. In cases when the plant is transgenic, the plant can be transformed with a vector containing any of the above described PPSRP coding nucleic acids, or the plant can be transformed with a promoter that directs expression of native PPSRP in the plant, for example. The invention provides that such a promoter can be tissue specific. Furthermore, such a promoter can be developmentally regulated. Alternatively, non-transgenic plants can have native PPSRP expression modified by inducing a native promoter. Furthermore, the invention provides that PPSRP expression can be modified by administration of an antisense molecule that inhibits expression of PPSRP.

The expression of Ppase-1 (SEQ ID NO:3) in target plants can be accomplished by, but is not limited to, one of the following examples: (a) constitutive promoter, (b) stress-inducible promoter, (c) chemical-induced promoter, and (d) engineered promoter over-expression with for example zinc-finger derived transcription factors (Greisman and Pabo, 1997 Science 275:657). The later case involves identification of the Ppase-1 (SEQ ID NO:3) homologues in the target plant as well as from its promoter. Zinc finger-containing recombinant transcription factors are engineered to specifically interact with the Ppase-1 (SEQ ID NO:3) homologue and transcription of the corresponding gene is activated.

As shown herein and described more fully below, expression of the PPSRP Ppase-1 (SEQ ID NO:3) in *Arabidopsis thaliana* confers a high degree of drought tolerance to the plant. Additionally, Ppase-1 (SEQ ID NO:3) confers tolerance to high salt concentrations to this plant.

In addition to introducing the PPSRP nucleic acid sequences into transgenic plants, these sequences can also be used to identify an organism as being *Physcomitrella patens* or a close relative thereof. Also, they may be used to identify the presence of *Physcomitrella patens* or a relative thereof in a mixed population of microorganisms. The invention provides the nucleic acid sequences of a number of *Physcomitrella patens* genes; by probing the extracted genomic DNA of a culture of a unique or mixed population of microorganisms under stringent conditions with a probe spanning a region of a *Physcomitrella patens* gene which is unique to this organism, one can ascertain whether this organism is present.

Further, the nucleic acid and protein molecules of the invention may serve as markers for specific regions of the genome. This has utility not only in the mapping of the genome, but also in functional studies of *Physcomitrella patens* proteins. For example, to identify the region of the genome to which a particular *Physcomitrella patens* DNA-binding protein binds, the *Physcomitrella patens* genome could be digested, and the fragments incubated with the DNA-binding protein. Those which bind the protein may be additionally probed with the nucleic acid molecules of the invention, preferably with readily detectable labels; binding of such a nucleic acid molecule to the genome fragment enables the localization of the fragment to the genome map of *Physcomitrella patens*, and, when performed multiple times with different enzymes, facilitates a rapid determination of the nucleic acid sequence to which the protein binds. Further, the nucleic acid molecules of the invention may be sufficiently homologous to the sequences of related species such that these nucleic acid molecules may serve as markers for the construction of a genomic map in related mosses.

The PPSRP nucleic acid molecules of the invention are also useful for evolutionary and protein structural studies. The metabolic and transport processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the protein which are essential for the functioning of the enzyme. This type of determination is of value for protein engineering studies and may give an indication of what the protein can tolerate in terms of mutagenesis without losing function.

Manipulation of the PPSRP nucleic acid molecules of the invention may result in the production of PPSRPs having functional differences from the wild-type PPSRPs. These proteins may be improved in efficiency or activity, may be present in greater numbers in the cell than is usual, or may be decreased in efficiency or activity.

There are a number of mechanisms by which the alteration of a PPSRP of the invention may directly affect stress response and/or stress tolerance. In the case of plants expressing PPSRPs, increased transport can lead to improved salt and/or solute partitioning within the plant tissue and organs. By either increasing the number or the activity of transporter molecules which export ionic molecules from the cell, it may be possible to affect the salt tolerance of the cell.

The effect of the genetic modification in plants, *C. glutamicum*, fungi, algae, or ciliates on stress tolerance can be assessed by growing the modified microorganism or plant under less than suitable conditions and then analyzing the growth characteristics and/or metabolism of the plant. Such analysis techniques are well known to one skilled in the art, and include dry weight, wet weight, protein synthesis, carbohydrate synthesis, lipid synthesis, evapotranspiration rates, general plant and/or crop yield, flowering, reproduction, seed setting, root growth, respiration rates, photosynthesis rates, etc. (Applications of HPLC in Biochemistry in: Laboratory Techniques in Biochemistry and Molecular Biology, vol. 17; Rehm et al., 1993 Biotechnology, vol. 3, Chapter III: Product recovery and purification, page 469–714, VCH: Weinheim; Belter, Pa. et al., 1988 Bioseparations: downstream processing for biotechnology, John Wiley and Sons; Kennedy, J. F. and Cabral, J. M. S., 1992 Recovery processes for biological materials, John Wiley and Sons; Shaeiwitz, J. A. and Henry, J. D., 1988 Biochemical separations, in: Ulmann's Encyclopedia of Industrial Chemistry, vol. B3, Chapter 11, page 1–27, VCH: Weinheim; and Dechow, F. J. (1989) Separation and purification techniques in biotechnology, Noyes Publications).

For example, yeast expression vectors comprising the nucleic acids disclosed herein, or fragments thereof, can be constructed and transformed into *Saccharomyces cerevisiae* using standard protocols. The resulting transgenic cells can then be assayed for fail or alteration of their tolerance to drought, salt, and temperature stress. Similarly, plant expression vectors comprising the nucleic acids disclosed herein, or fragments thereof, can be constructed and transformed into an appropriate plant cell such as *Arabidopsis*, soy, rape, maize, wheat, *Medicago truncatula*, etc., using standard protocols. The resulting transgenic cells and/or plants derived therefrom can then be assayed for fail or alteration of their tolerance to drought, salt, and temperature stress.

The engineering of one or more PPSRP genes of the invention may also result in PPSRPs having altered activities which indirectly impact the stress response and/or stress tolerance of algae, plants, ciliates or fungi or other microorganisms like *C. glutamicum*. For example, the normal biochemical processes of metabolism result in the production of a variety of products (e.g., hydrogen peroxide and other reactive oxygen species) which may actively interfere with these same metabolic processes (for example, peroxynitrite is known to nitrate tyrosine side chains, thereby inactivating some enzymes having tyrosine in the active site (Groves, J. T., 1999 Curr. Opin. Chem. Biol. 3(2):226–235). While these products are typically excreted, cells can be genetically altered to transport more products than is typical for a wild-type cell. By optimizing the activity of one or more PPSRPs of the invention which are involved in the export of specific molecules, such as salt molecules, it may be possible to improve the stress tolerance of the cell.

Additionally, the sequences disclosed herein, or fragments thereof, can be used to generate knockout mutations in the genomes of various organisms, such as bacteria, mammalian cells, yeast cells, and plant cells. (Girke, T., 1998 The Plant Journal 15:39–48). The resultant knockout cells can then be evaluated for their ability or capacity to tolerate various stress conditions, their response to various stress conditions, and the effect on the phenotype and/or genotype of the mutation. For other methods of gene inactivation include U.S. Pat. No. 6,004,804 "Non-Chimeric Mutational Vectors" and Puttaraju et al., 1999 Spliceosome-mediated RNA trans-splicing as a tool for gene therapy Nature Biotechnology 17:246–252.

The aforementioned mutagenesis strategies for PPSRPs to result in increased stress resistance are not meant to be limiting; variations on these strategies will be readily apparent to one skilled in the art. Using such strategies, and incorporating the mechanisms disclosed herein, the nucleic acid and protein molecules of the invention may be utilized to generate algae, ciliates, plants, fungi or other microorganisms like *C. glutamicum* expressing mutated PPSRP nucleic acid and protein molecules such that the stress tolerance is improved.

The present invention also provides antibodies which specifically bind to a PPSRP-polypeptide, or a portion thereof, as encoded by a nucleic acid disclosed herein or as described herein. Antibodies can be made by many well-known methods (See, e.g. *Harlow and Lane*, "Antibodies; A Laboratory Manual" Cold Spring Harbor Laboratory, Cold Spring Harbor, N.Y., (1988)). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced. (See, for example, Kelly et al., 1992 Bio/Technology 10:163–167; Bebbington et al., 1992 Bio/Technology 10:169–175).

The phrases "selectively binds" and "specifically binds" with the polypeptide refers to a binding reaction which is determinative of the presence of the protein in a heterogeneous population of proteins and other biologics. Thus, under designated immunoassay conditions, the specified antibodies bound to a particular protein do not bind in a significant amount to other proteins present in the sample. Selective binding to an antibody under such conditions may require an antibody that is selected for its specificity for a particular protein. A variety of immunoassay formats may be used to select antibodies selectively bind with a particular protein. For example, solid-phase ELISA immunoassays are routinely used to select antibodies selectively immunoreactive with a protein. See *Harlow and Lane* "Antibodies, A Laboratory Manual" Cold Spring Harbor Publications, New York, (1988), for a description of immunoassay formats and conditions that could be used to determine selective binding.

In some instances, it is desirable to prepare monoclonal antibodies from various hosts. A description of techniques for preparing such monoclonal antibodies may be found in Stites et al., editors, "Basic and Clinical Immunology," (Lange Medical Publications, Los Altos, Calif., Fourth Edition) and references cited therein, and in Harlow and Lane ("Antibodies, A Laboratory Manual" Cold Spring Harbor Publications, New York, 1988).

Throughout this application various publications are referenced The disclosures of all of these publications and those references cited within those publications in their entireties are hereby incorporated by reference into this application in order to more filly describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims. Additionally, all references cited herein are hereby expressly incorporated herein by reference.

EXAMPLES

Example 1

Growth of *Physcomitrella patens* Cultures

For this study, plants of the species *Physcomitrella patens* (Hedw.) B. S. G. from the collection of the genetic studies section of the University of Hamburg were used. They originate from the strain 16/14 collected by H. L. K. Whitehouse in Gransden Wood, Huntingdonshire (England), which was subcultured from a spore by Engel (1968, Am. J. Bot. 55, 438–446). Proliferation of the plants was carried out by means of spores and by means of regeneration of the gametophytes. The protonema developed from the haploid spore as a chloroplast-rich chloronema and chloroplast-low caulonema, on which buds formed after approximately 12 days. These grew to give gametophores bearing antheridia and archegonia. After fertilization, the diploid sporophyte with a short seta and the spore capsule resulted, in which the meiospores matured.

Culturing was carried out in a climatic chamber at an air temperature of 25° C. and light intensity of 55 micromol $s^{-1}$ $m^{-2}$ (white light; Philips TL 65W/25 fluorescent tube) and a light/dark change of 16/8 hours. The moss was either modified in liquid culture using Knop medium according to Reski and Abel (1985, Planta 165:354–358) or cultured on Knop solid medium using 1% oxoid agar (Unipath, Basingstoke, England). The protonemas used for RNA and DNA isolation were cultured in aerated liquid cultures. The protonemas were comminuted every 9 days and transferred to fresh culture medium.

Example 2

Total DNA Isolation from Plants

The details for the isolation of total DNA relate to the working up of one gram fresh weight of plant material. The materials used include the following buffers: CTAB buffer: 2% (w/v) N-cethyl-N,N,N-trinmethylammonium bromide (CTAB); 100 mM Tris HCl pH 8.0; 1.4 M NaCl; 20 mM EDTA, N-Laurylsarcosine buffer: 10% (w/v) N-laurylsarcosine; 100 mM Tris HCl pH 8.0; 20 mM EDTA.

The plant material was triturated under liquid nitrogen in a mortar to give a fine powder and transferred to 2 ml Eppendorf vessels. The frozen plant material was then covered with a layer of 1 ml of decomposition buffer (1 ml CTAB buffer, 100 µl of N-laurylcarcosine buffer, 20 µl of β-mercaptoethanol and 10 µl of proteinase K solution, 10 mg/ml) and incubated at 60° C. for one hour with continuous shaking. The homogenate obtained was distributed into two Eppendorf vessels (2 ml) and extracted twice by shaking with the same volume of chloroform/isoamyl alcohol (24:1). For phase separation, centrifugation was carried out at 8000×g and room temperature for 15 minutes in each case. The DNA was then precipitated at −70° C. for 30 minutes using ice-cold isopropanol. The precipitated DNA was sedimented at 4° C. and 10,000 g for 30 minutes and resuspended in 180 µl of TE buffer (Sambrook et al., 1989, Cold Spring Harbor Laboratory Press: ISBN 0-87969-309-6). For further purification, the DNA was treated with NaCl (1.2 M final concentration) and precipitated again at −70° C. for 30 minutes using twice the volume of absolute ethanol. After a washing step with 70% ethanol, the DNA was dried and subsequently taken up in 50 µl of $H_2O$+RNAse (50 mg/ml final concentration). The DNA was dissolved overnight at 4° C. and the RNAse digestion was subsequently carried out at 37° C. for 1 hour. Storage of the DNA took place at 4° C.

Example 3

Isolation of Total RNA and Poly-(A)+ RNA and cDNA Library Construction from *Physcomitrella patens*

For the investigation of transcripts, both total RNA and poly-(A)$^+$ RNA were isolated. The total RNA was obtained from wild-type 9 day old protonemata following the GTC-method (Reski et al. 1994, Mol. Gen. Genet., 244:352–359). The Poly(A)+ RNA was isolated using Dyna Beads$^R$ (Dynal, Oslo, Norway) following the instructions of the manufacturers protocol. After determination of the concentration of the RNA or of the poly(A)+ RNA, the RNA was precipitated by addition of 1/10 volumes of 3 M sodium acetate pH 4.6 and 2 volumes of ethanol and stored at −70° C.

For cDNA library construction, first strand synthesis was achieved using Murine Leukemia Virus reverse transcriptase (Roche, Mannheim, Germany) and oligo-d(T)primers, second strand synthesis by incubation with DNA polymerase I, Klenow enzyme and RNAseH digestion at 12° C. (2 hours), 16° C. (1 hour) and 22° C. (1 hour). The reaction was stopped by incubation at 65° C. (10 minutes) and subsequently transferred to ice. Double stranded DNA molecules were blunted by T4-DNA-polymerase (Roche, Mannheim) at 37° C. (30 minutes). Nucleotides were removed by phenol/chloroform extraction and Sephadex G50 spin columns. EcoRI adapters (Pharmacia, Freiburg, Germany) were ligated to the cDNA ends by T4-DNA-ligase (Roche, 12° C., overnight) and phosphorylated by incubation with polynucleotide kinase (Roche, 37° C., 30 minutes). This mixture was subjected to separation on a low melting agarose gel. DNA molecules larger than 300 base pairs were eluted from the gel, phenol extracted, concentrated on Elutip-D-columns (Schleicher and Schuell, Dassel, Germany) and were ligated to vector arms and packed into lambda ZAPII phages or lambda ZAP-Express phages using the Gigapack Gold Kit (Stratagene, Amsterdam, Netherlands) using material and following the instructions of the manufacturer.

Example 4

Sequencing and Function Annotation of *Physcomitrella patens* ESTs cDNA libraries as described in Example 3 were used for DNA sequencing according to standard methods, and in particular, by the chain termination method using the ABI PRISM Big Dye Terminator Cycle Sequencing Ready Reaction Kit (Perkin-Elmer, Weiterstadt, Germany). Random Sequencing was carried out subsequent to preparative plasmid recovery from cDNA libraries via in vivo mass excision, retransformation, and subsequent plating of DH10B on agar plates (material and protocol details from Stratagene, Amsterdam, Netherlands. Plasmid DNA was prepared from overnight grown *E. coli* cultures grown in Luria-Broth medium containing ampicillin (see Sambrook et al. 1989 Cold Spring Harbor Laboratory Press: ISBN 0-87969-309-6) on a Qiagene DNA preparation robot (Qiagen, Hilden) according to the manufacturer's protocols. Sequencing primers with the following nucleotide sequences were used:

```
5'-CAGGAAACAGCTATGACC-3'      SEQ ID NO:4

5'-CTAAAGGGAACAAAAGCTG-3'     SEQ ID NO:5

5'-TGTAAAACGACGGCCAGT-3'      SEQ ID NO:6
```

Sequences were processed and annotated using the software package EST-MAX commercially provided by BioMax (Munich, Germany). The program incorporates practically all bioinformatics methods important for functional and structural characterization of protein sequences. For reference the website at pedandt.mips.biochem.de. The most important algorithms incorporated in EST-MAX are: FASTA: Very sensitive sequence database searches with estimates of statistical significance; Pearson W. R. (1990) Rapid and sensitive sequence comparison with FASTP and FASTA. Methods Enzymol. 183:63–98; BLAST: Very sensitive sequence database searches with estimates of statistical significance. Altschul S. F., Gish W., Miller W., Myers E. W., and Lipman D. J. Basic local alignment search tool. Journal of Molecular Biology 215:403–10; PREDATOR: High-accuracy secondary structure prediction from single and multiple sequences. Frishman, D. and Argos, P. (1997) 75% accuracy in protein secondary structure prediction. Proteins, 27:329–335; CLUSTALW: Multiple sequence alignment Thompson, J. D., Higgins, D. G. and Gibson, T. J. (1994) CLUSTAL W: improving the sensitivity of progressive multiple sequence alignment through sequence weighting, positions-specific gap penalties and weight matrix choice. Nucleic Acids Research, 22:4673–4680; TMAP: Transmembrane region prediction from multiply aligned sequences. Persson, B. and Argos, P. (1994) Prediction of transmembrane segments in proteins utilizing multiple sequence alignments. J. Mol. Biol. 237:182–192; ALOM2: Transmembrane region prediction from single sequences. Klein, P., Kanehisa, M., and DeLisi, C. Prediction of protein function from sequence properties: A discriminate analysis of a database. Biochim. Biophys. Acta 787:221–226 (1984). Version 2 by Dr. K. Nakai; PROSEARCH: Detection of PROSITE protein sequence patterns. Kolakowski L. F. Jr., Leunissen J. A. M., Smith J. E. (1992) ProSearch: fast searching of protein sequences with regular expression patterns related to protein structure and function. Biotechniques 13, 919–921; BLIMPS: Similarity searches against a database of ungapped blocks. J. C. Wallace and Henikoff S., (1992); PATMAT: A searching and extraction program for sequence, pattern and block queries and databases, CABIOS 8:249–254. Written by Bill Alford.

Example 5

Identification of *Physcomitrella patens* ORF Corresponding to PpPPase-1

The *Physcomitrella patens* partial cDNAs (ESTs) shown in Table 1 below were identified in the *Physcomitrella patens* EST sequencing program using the program EST-MAX through BLAST analysis. The Sequence Identification Numbers corresponding to these ESTs are as follows: PpPPase-1 (SEQ ID NO:1). The top hit of the BLAST is "inorganic Pyrophosphatase like protein" ORF from *Arabidopsis thaliana* (Swiss-Prot.-Accession-Number Q9LXC9). See also Table 2 for more details.

TABLE 1

| Functional Category | Function | Sequence Code | ORF position | Name |
|---|---|---|---|---|
| Phosphatase | inorganic pyrophosphatase | c_pp004077110r | 1048-35 | PpPPase-1 |

TABLE 2

Degree of amino acid identity and similarity of PpPpase-1 and other homologous proteins (GCG Gap program was used: gap penalty: 10; gap extension penalty 0.1; score matrix: blosum62)

| Swiss-Prot # | Q9LXC9 | P13998 | Q15181 | Q18680 | Q9PW32 |
|---|---|---|---|---|---|
| Protein name | Inorganic pyrophosphatase-like protein | Inorganic pyrophosphatase | Inorganic pyrophosphatase | Probable inorganic pyrophosphatase | Inorganic pyrophosphatase |
| specie | *Arabidopsis thaliana* (Mouse-ear cress) | *Kluyveromyces lactis* (Yeast) | *Homo sapiens* (Human) | *Caenorhabditis elegans* | *Torpedo marmorata* (Marbled electric ray) |
| Identity % | 66% | 34% | 32% | 35% | 33% |
| Similarity % | 73% | 42% | 42% | 43% | 42% |

Example 6

Cloning of the Full-length *Physcomitrella patens* cDNA Encoding for PpPPase-1

To isolate full-length PpPPase-1 (SEQ ID NO:2), PCR was performed with a gene-specific EST as the template DNA. The synthetic oligonucleotide primers (MWG-Biotech) for the reaction were:

```
RC025:
ATCCCGGGTGACAATGGCGGCAGCAAGAGCT          SEQ ID NO:7

RC026:
ATGAGCTCACACTAAACTCTAGCAAAAGTGAAG        SEQ ID NO:8
```

The primers designed contained a XmaI site in the 5' region and a SacI site in the 3' region for cloning purposes. The conditions for the reaction were standard conditions with PWO DNA polymerase (Roche). PCR was performed according to standard conditions and to manufacture's protocols (Sambrook et al. 1989, Biometra T3 Thermocycler). The parameters for the reaction were: five minutes at 94° C. followed by five cycles of one minute at 94° C., one minute at 50° C. and 1.5 minutes at 72° C. This was followed by twenty five cycles of one minute at 94° C., one minute at 65° C. and 1.5 minutes at 72° C. These parameters generated a fragment of 0.9 kilobases encoding the ORF of the PpPPase-1.

The fragment was extracted from agarose gel with a QIAquick Gel Extraction Kit (Qiagen) and ligated into the TOPO pCR 2.1 vector (Invitrogen) following manufacture's instructions. Recombinant vectors were transformed into Top10 cells (Invitrogen) using standard conditions (Sambrook et al. 1989). Transformed cells were selected for on LB agar containing 100 μg/ml carbenicillin, 0.8 mg X-gal (5-bromo-4-chloro-3-indolyl-β-D-galactoside) and 0.8 mg IPTG (isopropylthio-β-D-galactoside) grown overnight at 37° C. White colonies were selected and used to inoculate 3 ml of liquid LB containing 100 μg/ml ampicillin and grown overnight at 37° C. Plasmid DNA was extracted using the QIAprep Spin Miniprep Kit (Qiagen) following manufacture's instructions. Analyses of subsequent clones and restriction mapping was performed according to standard molecular biology techniques (Sambrook et al. 1989).

Example 7

Engineering Stress-tolerant *Arabidopsis* Plants by Overexpressing the Gene PpPPase-1

Binary Vector Construction: pGMSG

The pLMNC53 (Mankin, 2000, PhD thesis) vector was digested with HindIII (Roche) and blunt-end filled with Klenow enzyme and 0.1 mM dNTPs (Roche) according to manufacturer's instructions. This fragment was extracted from agarose gel with a QIAquick Gel Extraction Kit (Qiagen) according to manufacturer's instructions. The purified fragment was then digested with EcoRI (Roche) according to manufacturer's instructions. This fragment was extracted from agarose gel with a QIAquick Gel Extraction Kit (Qiagen) according to manufacturer's instructions. The resulting 1.4 kilobase fragment, the gentamycin cassette, included the nos promoter, aacCI gene and the g7 terminator.

The vector pBlueScript was digested with EcoRI and SmaI (Roche) according to manufacturer's instructions. The resulting fragment was extracted from agarose gel with a QIAquick Gel Extraction Kit (Qiagen) according to manufacturer's instructions. The digested pBlueScript vector and the gentamycin cassette fragments were ligated with T4 DNA Ligase (Roche) according to manufacturer's instructions, joining the two respective EcoRI sites and joining the blunt-ended HindIII site with the SmaI site.

The recombinant vector (pGMBS) was transformed into Top10 cells (Invitrogen) using standard conditions. Transformed cells were selected for on LB agar containing 100 µg/ml carbenicillin, 0.8 mg X-gal (5-bromo-4-chloro-3-indolyl-β-D-galactoside) and 0.8 mg IPTG (isopropylthio-β-D-galactoside), grown overnight at 37° C. White colonies were selected and used to inoculate 3 ml of liquid LB containing 100 µg/ml ampicillin and grown overnight at 37° C. Plasmid DNA was extracted using the QIAprep Spin Miniprep Kit (Qiagen) following manufacturer's instructions. Analyses of subsequent clones and restriction mapping was performed according to standard molecular biology techniques (Sambrook et al., 1989 Molecular Cloning, A Laboratory Manual. 2nd Edition. Cold Spring Harbor Laboratory Press. Cold Spring Harbor, N.Y.).

Subcloning of PpPPase-1 into the Binary Vector

The fragment containing the *Physcomitrella patens* Pyrophosphatase (PpPPase-1) was excised from the recombinant PCR2.1 TOPO vector by digestion with SacI and XmaI (Roche) according to manufacture's instructions. The subsequence fragment was excised from agarose gel with a QIAquick Gel Extraction Kit (QIAgen) according to manufacture's instructions and ligated into the binary vectors pGMSG, cleaved with XmaI and Ecl136II and dephosphorylated prior to ligation. The resulting recombinant pGMSG contained the PpPPase-1 in the sense orientation under the constitutive super promoter.

*Agrobacterium* Transformation

The recombinant vectors were transformed into *Agrobacterium tumefaciens* C58C1 and PMP90 according to standard conditions (Hoefgen and Willmitzer, 1990).

Plant Transformation

*Arabidopsis thaliana* ecotype C24 were grown and transformed according to standard conditions (Bechtold 1993, Acad. Sci. Paris. 316:1194–1199; Bent et al. 1994, Science 265:1856–1860).

Screening of Transformed Plants

T1 seeds were sterilized according to standard protocols (Xiong et al. 1999, Plant Molecular Biology Reporter 17: 159–170). Seeds were plated on ½ MS 0.6% agar supplemented with 1% sucrose, 150 µg/ml gentamycin (Sigma-Aldrich) and 2 µg/ml benomyl (Sigma-Aldrich). Seeds on plates were vernalized for four days at 4° C. The seeds were germinated in a climatic chamber at an air temperature of 22° C. and light intensity of 40 micromols$^{-1m2}$ (white light; Philips TL 65W/25 fluorescent tube) and 16 hours light and 8 hours dark day length cycle. Transformed seedlings were selected after 14 days and transferred to ½ MS 0.6% agar plates supplemented with 1% sucrose and allowed to recover for five-seven days.

Drought Tolerance Screening

T1 seedlings were transferred to dry, sterile filter paper in a petri dish and allowed to desiccate for two hours at 80% RH (relative humidity) in a Sanyo Growth Cabinet MLR-350H, micromol s$^{-1}$m$^{-2}$ (white light; Philips TL 65W/25 fluorescent tube). The RH was then decreased to 60% and the seedlings were desiccated further for eight hours. Seedlings were then removed and placed on ½ MS 0.6% agar plates supplemented with 2 µg/ml benomyl and scored after five days.

PpPPase-1 over-expressing lines showed a survival rate of 100% (23 survivors from 23 stressed plants), whereas only 21% of the untransformed controls survived. It is noteworthy that the analyses of these transgenic lines were performed with T1 plants, therefore, the results will be better when a homozygous, strong expresser is found.

Salt Tolerance Screening

Seedlings were transferred to filter paper soaked in ½ MS and placed on ½ MS 0.6% agar supplemented with 2 µg/ml benomyl the night before the salt tolerance screening. For the salt tolerance screening, the filter paper with the seedlings was moved to stacks of sterile filter paper, soaked in 50 mM NaCl, in a petri dish. After two hours, the filter paper with the seedlings was moved to stacks of sterile filter paper, soaked with 200 mM NaCl, in a petri dish. After two hours, the filter paper with the seedlings was moved to stacks of sterile filter paper, soaked in 600 mM NaCl, in a petri dish. After 10 hours, the seedlings were moved to petri dishes containing ½ MS 0.6% agar supplemented with 2 µg/ml benomyl. The seedlings were scored after 5 days.

Under salt stress conditions, PpPPase-1 over-expressing lines showed a survival rate of 27% (6 survivors from 22 stressed plants), whereas only 10% of the untransformed controls survived. It is noteworthy that the analyses of these transgenic lines were performed with T1 plants, therefore, the results will be better when a homozygous, strong expresser is found.

Freezing Tolerance Screening

Seedlings were moved to petri dishes containing ½ MS 0.6% agar supplemented with 2% sucrose and 2 µg/ml benomyl. After four days, the seedlings were incubated at 4° C. for 1 hour and then covered with shaved ice. The seedlings were then placed in an Environmental Specialist ES2000 Environmental Chamber and incubated for 3.5 hours beginning at −1.0° C. decreasing −1° C. per hour. The seedlings were then incubated at −5.0° C. for 24 hours and then allowed to thaw at 5° C. for 12 hours. The water was poured off and the seedlings were scored after 5 days. The transgenic plants are then screened for their improved cold tolerance demonstrating that transgene expression confers cold tolerance.

Example 8

Detection of the PpPPase-1 Transgene in the Transgenic *Arabidopsis* Lines

One leaf from a wild type and a transgenic *Arabidopsis* plant was homogenized in 250 µl Hexadecyltrimethyl ammonium bromide (CTAB) buffer (2% CTAB, 1.4 M NaCl, 8 mM EDTA and 20 mM Tris pH 8.0) and 1 µl β-mercaptoethanol. The samples were incubated at 60–65° C. for 30 minutes and 250 µl of Chloroform was then added to each sample. The samples were vortexed for 3 minutes and centrifuged for 5 minutes at 18,000×g. The supernatant was taken from each sample and 150 µl isopropanol was added. The samples were incubated at room temperature for 15 minutes, and centrifuged for 10 minutes at 18,000×g. Each pellet was washed with 70% ethanol dried, and resuspended in 20 µl TE. 4 µl of above suspension was used in a 20 µl PCR reaction using Taq DNA polymerase (Roche Molecular Biochemicals) according to the manufacturer's instructions. The primers used in the reactions were:

```
                                              SEQ ID NO:9
    5'GAATAGATACGCTGACACGC 3'

SEQ ID NO:10
    5'ATGAGCTGACACTAAACTCTAGCAAAACTGAAG 3'
```

The PCR program was as following: 1 cycle of 1 minute at 94° C., 1 minute at 75° C. and 3 minutes at 72° C., followed by 14 cycles of the same cycle except that the annealing temperature decreased 1° C. every cycle until 62° C.; and then 16 cycles of 1 minute at 94° C., 1 minute at 62° C. and 3 minutes at 72° C. A 1.3 kb fragment was generated from the positive control and the T1 transgenic plants. Binary vector plasmid with PpPPase-1 gene cloned in pGMSG was used as positive control and the wild type C24 genomic DNA was used as negative control in the PCR reactions. 10 μl PCR reaction was analyzed on 0.8% agarose—ethidium bromide gel.

Example 9

Detection of the PpPPase-1 Transgene mRNA in Transgenic *Arabidopsis* Lines

Transgene expression was detected using RT-PCR. Total RNA was isolated from stress-treated plants using a procedure adapted from (Verwoerd et al., 1989 NAR 17:2362). Leaf samples (50–100 mg) were collected and ground to a fine powder in liquid nitrogen. Ground tissue was resuspended in 500 μl of a 80° C., 1:1 mixture, of phenol to extraction buffer (100 mM LiCl, 100 mM Tris pH8, 10 mM EDTA, 1% SDS), followed by brief vortexing to mix. After the addition of 250 μl of chloroform, each sample was vortexed briefly. Samples were then centrifuged for 5 minutes at 12,000×g. The upper aqueous phase was removed to a fresh eppendorf tube. RNA was precipitated by adding $^{1}/_{10}{}^{th}$ volume 3M sodium acetate and 2 volumes 95% ethanol. Samples were mixed by inversion and placed on ice for 30 minutes. RNA was pelleted by centrifugation at 12,000×g for 10 minutes. The supernatant was removed and pellets briefly air-dried. RNA sample pellets were resuspended in 10 μl DEPC treated water. To remove contaminating DNA from the samples, each was treated with RNase-free DNase (Roche) according to the manufacturer's recommendations. cDNA was synthesized from total RNA using the 1$^{st}$ Strand cDNA synthesis kit (Boehringer Mannheim) following manufacturer's recommendations. PCR amplification of a 350 base pair fragment from the synthesized cDNA was performed using Taq DNA polymerase (Roche) and primers designed specifically for PpPPase-1 in the following reaction: 1×PCR buffer, 1.5 mM MgCl2, 0.2 μM each primer, 0.2 μM dNTPs, 1 unit polymerase, 5 μl cDNA from synthesis reaction. The following primer combination was used:

```
RC870: 5'GCAGAGTATACCGTCAAGGAGGAAG3'   SEQ ID NO:11

RC871: 5'GGCTTGCCTCTCCCCAATTTCAACA3'   SEQ ID NO:12
```

Amplification was performed under the following conditions: Denaturation, 95° C., 1 minute; annealing, 62° C., 30 seconds; extension, 72° C., 1 minute, 35 cycles; extension, 72° C., 5 minutes; hold, 4° C., forever. PCR products were run on a 1% agarose gel, stained with ethidium bromide, and visualized under UV light using the Quantity-One gel documentation system (Bio-Rad).

Expression of the transgenes was detected in the T1 transgenic line. These results indicated that the transgenes are expressed in the transgenic lines and strongly suggested that their gene product improved plant stress tolerance in the transgenic lines. In agreement with the previous statement, no expression of identical or very similar endogenous genes could be detected by this method. These results are in agreement with the data from Example 7.

Example 10

Engineering Stress-tolerant Soybean Plants by Over-expressing the PpPPase-1 Gene The clone PpPPase-1 (SEQ ID NO:2) is used to transform soybean as described below.

Seeds of soybean are surface sterilized with 70% ethanol for 4 minutes at room temperature with continuous shaking, followed by 20% (v/v) Clorox supplemented with 0.05% (v/v) Tween for 20 minutes with continuous shaking. Then, the seeds are rinsed 4 times with distilled water and placed on moistened sterile filter paper in a Petri dish at room temperature for 6 to 39 hours. The seed coats are peeled off, and cotyledons are detached from the embryo axis. The embryo axis is examined to make sure that the meristematic region is not damaged. The excised embryo axes are collected in a half-open sterile Petri dish and air-dried to a moisture content less than 20% (fresh weight) in a sealed Petri dish until further use.

*Agrobacterium tumefaciens* culture is prepared from a single colony in LB solid medium plus appropriate antibiotics (e.g. 100 mg/l streptomycin, 50 mg/l kanamycin) followed by growth of the single colony in liquid LB medium to an optical density at 600 mn of 0.8. Then, the bacterial culture is pelleted at 7000 rpm for 7 minutes at room temperature, and resuspended in MS (Murashige and Skoog, 1962) medium supplemented with 100 μM acetosyringone. Bacterial cultures are incubated in this pre-induction medium for 2 hours at room temperature before use. The axes of soybean zygotic seed embryos at approximately 15% moisture content are imbibed for 2 hours at room temperature with the pre-induced *Agrobacterium* suspension cuhure. The embryos are removed from the imbibition culture and are transferred to Petri dishes containing solid MS medium supplemented with 2% sucrose and incubated for 2 days, in the dark at room temperature. Alternatively, the embryos are placed on top of moistened (liquid MS medium) sterile filter paper in a Petri dish and incubated under the same conditions described above. After this period, the embryos are transferred to either solid or liquid MS medium supplemented with 500 mg/L carbenicillin or 300 mg/L cefotaxime to kill the agrobacteria. The liquid medium is used to moisten the sterile filter paper. The embryos are incubated for 4 weeks at 25° C., under 150 μmol m$^{-2}$sec$^{-1}$ and 12 hours photoperiod. Once the seedlings produced roots, they are transferred to sterile metromix soil. The medium of the in vitro plants is washed off before the plants are transferred to soil. The plants are kept under a plastic cover for 1 week to favor the acclimatization process. Then the plants are transferred to a growth room where they are incubated at 25° C., under 150 μmol m$^{-2}$sec$^{-1}$ light intensity and 12 hours photoperiod for about 80 days.

The transgenic plants are then screened for their improved drought, salt and/or cold tolerance according to the screening method described in Example 7 to demonstrate that transgene expression confers stress tolerance.

Example 11

Engineering Stress-tolerant Rapeseed/Canola Plants by Over-expressing the PpPPase-1 Gene The clone PpPPase-1 (SEQ ID NO:2) is used to transform rapeseed/canola as described below.

The method of plant transformation described herein is also applicable to Brassica and other crops. Seeds of canola are surface sterilized with 70% ethanol for 4 minutes at room temperature with continuous shaking, followed by 20% (v/v) Clorox supplemented with 0.05% (v/v) Tween for 20 minutes, at room temperature with continuous shaking. Then, the seeds are rinsed 4 times with distilled water and placed on moistened sterile filter paper in a Petri dish at room temperature for 18 hours. Then the seed coats are removed and the seeds are air dried overnight in a half-open sterile Petri dish. During this period, the seeds lose approx. 85% of its water content. The seeds are then stored at room temperature in a sealed Petri dish until further use. DNA constructs and embryo imbibition are as described in Example 10. Samples of the primary transgenic plants (T0) are analyzed by PGR to confirm the presence of T-DNA. These results are confirmed by Southern hybridization in which DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labelled probe by PCR, and used as recommended by the manufacturer.

The transgenic plants are then screened for their improved stress tolerance according to the screening method described in Example 7 demonstrating that transgene expression confers drought tolerance.

Example 12

Engineering Stress-tolerant Corn Plants by Over-expressing the PpPPase-1 Gene

The clone PpPPase-1 (SEQ ID NO:2) is used to transform soybean as described below.

Transformation of maize (*Zea Mays* L.) is performed with the method described by Ishida et al. 1996. Nature Biotch 14745–50. Immature embryos are co-cultivated with *Agrobacterium tumefaciens* that carry "super binary" vectors, and transgenic plants are recovered through organogenesis. This procedure provides a transformation efficiency of between 2.5% and 20%. The transgenic plants are then screened for their improved drought, salt and/or cold tolerance according to the screening method described in Example 7 demonstrating that transgene expression confers stress tolerance.

Example 13

Engineering Stress-tolerant Wheat Plants by Over-expressing the PpPPase-1 Gene

The clone PpPPase-1 (SEQ ID NO:2) is used to transform soybean as described below.

Transformation of wheat is performed with the method described by Ishida et al. 1996 Nature Biotch 14745–50. Immature embryos are co-cultivated with *Agrobacterium tumefaciens* that carry "super binary" vectors, and transgenic plants are recovered through organogenesis. This procedure provides a transformation efficiency between 2.5% and 20%. The transgenic plants are then screened for their improved stress tolerance according to the screening method described in Example 7 demonstrating that transgene expression confers drought tolerance.

Example 14

Identification of Homologous and Heterologous Genes

Gene sequences can be used to identify homologous or heterologous genes from cDNA or genomic libraries. Homologous genes (e.g. full-length cDNA clones) can be isolated via nucleic acid hybridization using for example cDNA libraries. Depending on the abundance of the gene of interest, 100,000 up to 1,000,000 recombinant bacteriophages are plated and transferred to nylon membranes. After denaturation with alkali, DNA is immobilized on the membrane by e.g. UV cross linking. Hybridization is carried out at high stringency conditions. In aqueous solution hybridization and washing is performed at an ionic strength of 1 M NaCl and a temperature of 68° C. Hybridization probes are generated by e.g. radioactive ($^{32}$P) nick transcription labeling (High Prime, Roche, Mannheim, Germany). Signals are detected by autoradiography.

Partially homologous or heterologous genes that are related but not identical can be identified in a manner analogous to the above-described procedure using low stringency hybridization and washing conditions. For aqueous hybridization, the ionic strength is normally kept at 1 M NaCl while the temperature is progressively lowered from 68 to 42° C.

Isolation of gene sequences with homologies (or sequence identity/similarity) only in a distinct domain of (for example 10–20 amino acids) can be carried out by using synthetic radio labeled oligonucleotide probes. Radio labeled oligonucleotides are prepared by phosphorylation of the 5-prime end of two complementary oligonucleotides with T4 polynucleotide kinase. The complementary oligonucleotides are annealed and ligated to form concatemers. The double stranded concatemers are than radiolabeled by, for example, nick transcription Hybridization is normally performed at low stringency conditions using high oligonucleotide concentrations.

Oligonucleotide Hybridization Solution:
6×SSC
0.01 M sodium phosphate
1 mM EDTA (pH 8)
0.5% SDS
100 µg/ml denatured salmon sperm DNA
0.1% nonfat dried milk During hybridization, temperature is lowered stepwise to 5–10° C. below the estimated oligonucleotide Tm or down to room temperature followed by washing steps and autoradiography. Washing is performed with low stringency such as 3 washing steps using 4×SSC. Further details are described by Sambrook, J. et al. (1989), "Molecular Cloning: A Laboratory Manual", Cold Spring Harbor Laboratory Press or Ausubel, F. M. et al. (1994) "Current Protocols in Molecular Biology", John Wiley & Sons.

Example 15

Identification of Homologous Genes by Screening Expression Libraries with Antibodies c-DNA clones can be used to produce recombinant protein for example in *E. coli* (e.g. Qiagen QIAexpress pQE system). Recombinant proteins are then normally affinity purified via Ni-NTA affinity chromatography (Qiagen).

Recombinant proteins are then used to produce specific antibodies for example by using standard techniques for rabbit immunization. Antibodies are affinity purified using a Ni-NTA column saturated with the recombinant antigen as described by Gu et al., 1994 BioTechniques 17:257–262. The antibody can than be used to screen expression cDNA libraries to identify homologous or heterologous genes via an immunological screening (Sambrook, J. et al. (1989), "Molecular Cloning: A Laboratory Manual", Cold Spring Harbor Laboratory Press or Ausubel, F. M. et al. (1994) "Current Protocols in Molecular Biology", John Wiley & Sons).

Example 16

In vivo Mutagenesis

In vivo mutagenesis of microorganisms can be performed by passage of plasmid (or other vector) DNA through E. coli or other microorganisms (e.g. Bacillus spp. or yeasts such as Saccharomyces cerevisiae) which are impaired in their capabilities to maintain the integrity of their genetic information. Typical mutator stains have mutations in the genes for the DNA repair system (e.g., mutHLS, mutd, mutT, etc.; for reference, see Rupp, W. D. (1996) DNA repair mechanisms, in: Escherichia coli and Salmonella, p. 2277–2294, ASM: Washington.) Such strains are well known to those skilled in the art. The use of such strains is illustrated, for example, in Greener, A. and Callahan, M. (1994) Strategies 7: 32–34. Transfer of mutated DNA molecules into plants is preferably done after selection and testing in microorganisms. Transgenic plants are generated according to various examples within the exemplification of this document.

Example 17

In Vitro Analysis of the Function of Physcomitrella Genes in Transgenic Organisms The determination of activities and kinetic parameters of enzymes is well established in the art. Experiments to determine the activity of any given altered enzyme must be tailored to the specific activity of the wild-type enzyme, which is well within the ability of one skilled in the art. Overviews about enzymes in general, as well as specific details concerning structure, kinetics, principles, methods, applications and examples for the determination of many enzyme activities may be found, for example, in the following references: Dixon, M., and Webb, E. C., (1979) Enzymes. Longmans: London; Fersht, (1985) Enzyme Structure and Mechanism. Freeman: New York; Walsh, (1979) Enzymatic Reaction Mechanisms. Freeman: San Francisco; Price, N. C., Stevens, L. (1982) Fundamentals of Enzymology. Oxford Univ. Press: Oxford; Boyer, P. D., ed. (1983) The Enzymes, 3$^{rd}$ ed. Academic Press: New York; Bisswanger, H., (1994) Enzymkinetik, 2$^{nd}$ ed. VCH: Weinheim (ISBN 3527300325); Bergmeyer, H. U., Bergmeyer, J., Graβl, M., eds. (1983–1986) Methods of Enzymatic Analysis, 3$^{rd}$ ed., vol. I–XII, Verlag Chemie: Weinheim; and Ullmann's Encyclopedia of Industrial Chemistry (1987) vol. A9, Enzymes. VCH: Weinheim, p. 352–363.

The activity of proteins which bind to DNA can be measured by several well-established methods, such as DNA band-shift assays (also called gel retardation assays). The effect of such proteins on the expression of other molecules can be measured using reporter gene assays (such as that described in Kolmar, H. et al. (1995) EMBO J. 14: 3895–3904 and references cited therein). Reporter gene test systems are well known and established for applications in both pro- and eukaryotic cells, using enzymes such as β-galactosidase, green fluorescent protein, and several others.

The determination of activity of membrane-transport proteins can be performed according to techniques such as those described in Gennis, R. B. Pores, Channels and Transporters, in Biomembranes, Molecular Structure and Function, pp. 85–137, 199–234 and 270–322, Springer: Heidelberg (1989).

Example 18

Purification of the Desired Product from Transformed Organisms

Recovery of the desired product from plant material (i.e., Physcomitrella patents or Arabidopsis thaliana), fungi, algae, ciliates, C. glutamicum cells, or other bacterial cells transformed with the nucleic acid sequences described herein, or the supernatant of the above-described cultures can be performed by various methods well known in the art. If the desired product is not secreted from the cells, can be harvested from the culture by low-speed centrifugation, the cells can be lysed by standard techniques, such as mechanical force or sonification. Organs of plants can be separated mechanically from other tissue or organs. Following homogenization cellular debris is removed by centrifugation, and the supernatant fraction containing the soluble proteins is retained for further purification of the desired compound. If the product is secreted from desired cells, then the cells are removed from the culture by low-speed centrifugation, and the supernate fraction is retained for further purification.

The supernatant fraction from either purification method is subjected to chromatography with a suitable resin, in which the desired molecule is either retained on a chromatography resin while many of the impurities in the sample are not, or where the impurities are retained by the resin while the sample is not. Such chromatography steps may be repeated as necessary, using the same or different chromatography resins. One skilled in the art would be well-versed in the selection of appropriate chromatography resins and in their most efficacious application for a particular molecule to be purified. The purified product may be concentrated by filtration or ultrafiltration, and stored at a temperature at which the stability of the product is maximized.

There is a wide array of purification methods known to the art and the preceding method of purification is not meant to be limiting. Such purification techniques are described, for example, in Bailey, J. E. & Ollis, D. F. Biochemical Engineering Fundamentals, McGraw-Hill: New York (1986). Additionally, the identity and purity of the isolated compounds may be assessed by techniques standard in the art. These include high-performance liquid chromatography (HPLC), spectroscopic methods, staining methods, thin layer chromatography, NIRS, enzymatic assay, or microbiologically. Such analysis methods are reviewed in: Patek et al., 1994 Appl. Environ. Microbiol. 60:133–140; Malakhova et al., 1996 Biotekhnologiya 11:27–32; and Schmidt et al., 1998 Bioprocess Engineer. 19:67–70. Ulmann's Encyclopedia of Industrial Chemistry, (1996) vol. A27, VCH: Weinheim, p. 89–90, p. 521–540, p. 540–547, p. 559–566, 575–581 and p. 581–587; Michal, G. (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, vol. 17.

SEQUENCE LISTING

<160> NUMBER OF SEQ ID NOS: 12

<210> SEQ ID NO 1
<211> LENGTH: 1243
<212> TYPE: DNA
<213> ORGANISM: Physcomitrella patens
<220> FEATURE:
<221> NAME/KEY: modified_base
<222> LOCATION: (1182)
<223> OTHER INFORMATION: "n" represents a, t, c, g, other or unknown
<220> FEATURE:
<221> NAME/KEY: modified_base
<222> LOCATION: (1218)
<223> OTHER INFORMATION: "n" represents a, t, c, g, other or unknown

<400> SEQUENCE: 1

```
aacaccaccc cacagaggag ttcgaagagg aactaaacga gggaaagttc tccagctgga      60
acgctcctct tcacgaggtt tgcccatgca ttgttggtct cttcaatgac cttcagtgca     120
taatccttat cagcaggctt gttatcaaga ccaaacctat tggcgggctt ccatcgggg     180
atcttgtaat ctctgaacca gtctctaatt gcggtcaaag tgcctgggaa gtgcttctcg     240
caatcagcca cgttgttgac cagatcagcc ttgggatcgt cgatggagat agccacaact     300
ttccagtcaa gttcaccctc gtcaatcatg ctaaaaccg gatgggttt cacctttaag     360
acttctccaa ttttggcttg cctctcccca atttcaacaa cgtcaactgg gtcgttgtca     420
ccgaacgcgt tctccacgtc agagttagag tgcgaagggt cctcccatgt ctggggaaga     480
agtccgtaat tccagttgat gttataaggg tagaaccgga gcttcccctt cttcgtgtcc     540
tgcttgatgg gagtgctggg ctcctcagtc gcaacctcca tcttagcact agtctcctta     600
gggatctcaa caacgaagtt gtagagtccg tctccggcgt ggaggggat atcatgccat     660
ggtgagatcg tcttgccaga cttgtcagag aagaagaccc tgtactctag agactcagct     720
gctccttcct ccttgacggt atactctgca gagacgacct tacagacctg gaatctcctg     780
ctcttcacag cagacctctg cacgaaagat tggtgcagtg gggctgccct caaggagagg     840
gaagcagcag gcaacaatgc cgtcctctgt gaacccttca ccactgatga gttcacgcac     900
tgtggcaaat gggacacgca ccctgctgcc atagctcttg ctgccgccat tgtcacctgc     960
tgcgatgcaa ccttgcggac accgcacgac gagaactgag agcacgagag agcgagcgag    1020
agacagagac gcaagcagat ttcgatgtcc tagtccagga ccctcccgt cggagtttag    1080
tgtgtggtgc ctgatgaacc agtgcatctg gactcactaa aaacgaatat gctccgtttt    1140
agtgacttac taatcctaac ttacaaactt tctcgcagcg tncccatggg cctgctgaat    1200
gcctaagatg ctacgttncc cgtgtgggga gctcatctgg tgc                      1243
```

<210> SEQ ID NO 2
<211> LENGTH: 1498
<212> TYPE: DNA
<213> ORGANISM: Physcomitrella patens

<400> SEQUENCE: 2

```
gaattcggca ccaggtcgtg cggtgtccgc aaggttgcat cgcagcaggt gacaatggcg      60
gcagcaagag ctatggcagc agggtgcgtg tcccatttgc cacagtgcgt gaactcatca     120
gtggtgaagg gttcacagag gacggcattg ttgcctgctg cttccctctc cttgagggca     180
gccccactgc accaatcttt cgtgcagagg tctgctgtga agagcaggag attccaggtc     240
tgtaaggtcg tctctgcaga gtataccgtc aaggaggaag gagcagctga gtctctagag     300
```

```
tacagggtct tcttctctga caagtctggc aagacgatct caccatggca tgatatcccc      360
ctccacgccg agacggact  ctacaacttc gttgttgaga tccctaagga gactagtgct      420
aagatggagg ttgcgactga ggagcccagc actcccatca agcaggacac gaagaagggg      480
aagctccggt tctaccctta aacatcaac  tggaattacg acttcttcc  ccagacatgg      540
gaggaccctt cgcactctaa ctctgacgtg gagaacgcgt tcggtgacaa cgacccagtt      600
gacgttgttg aaattgggga gaggcaagcc aaaattggag aagtccttaa ggtgaaaccc      660
atcgcggttt tagccatgat tgacgagggt gaacttgact ggaaagttgt ggctatctcc      720
atcgacgatc ccaaggctga tctggtcaac aacgtggctg attgcgagaa gcacttccca      780
ggcactttga ccgcaattag agactggttc agagattaca agatccccga tggaaagccc      840
gccaataggt ttggtcttga taacaagcct gctgataagg attatgcact gaaggtcatt      900
gaagagacca acaatgcatg gcaaaacctc gtgaagagga gcgttccagc tggagaactt      960
tccctcgttt agttcctctt cgaactcctc tgtgggtggt gttgttcaat ctggcaacca     1020
gattacatca aacacgatt  agctcttacg gaaacttcag ttttgctaga gtttagtgtt     1080
ccaacatttg taccttgtat ctcttggttt ccgagaattt gataactcct agaatcaatt     1140
gattgcagcg taagcagcag ctttgtaact ttgtgggtcg tcattgcatt gaccgttctc     1200
ctgcgaggac aagagctgtt agaagtatct tgttgtggta acatgtgcct ccctgcaacc     1260
tagattccac agtttgcatg agtcattgat ataatgtagc agattattcc agtggctttt     1320
tgctcgttcg ctacagcgtt atcttgagac agaatgatca atcctcttct tagaacgtta     1380
gtactggctg aacttggcaa ttgctttatt attaaacacg tgaaggctta ttgccaagtt     1440
tatcaataaa caaagcattg tatcctaaaa aaaaaaaaaa aaaaaaaaaa aactcgag       1498
```

<210> SEQ ID NO 3
<211> LENGTH: 305
<212> TYPE: PRT
<213> ORGANISM: Physcomitrella patens

<400> SEQUENCE: 3

```
Met Ala Ala Ala Arg Ala Met Ala Ala Gly Cys Val Ser His Leu Pro
1               5                   10                  15

Gln Cys Val Asn Ser Ser Val Val Lys Gly Ser Gln Arg Thr Ala Leu
            20                  25                  30

Leu Pro Ala Ala Ser Leu Ser Leu Arg Ala Ala Pro Leu His Gln Ser
        35                  40                  45

Phe Val Gln Arg Ser Ala Val Lys Ser Arg Arg Phe Gln Val Cys Lys
    50                  55                  60

Val Val Ser Ala Glu Tyr Thr Val Lys Glu Glu Gly Ala Ala Glu Ser
65                  70                  75                  80

Leu Glu Tyr Arg Val Phe Phe Ser Asp Lys Ser Gly Lys Thr Ile Ser
                85                  90                  95

Pro Trp His Asp Ile Pro Leu His Ala Gly Asp Gly Leu Tyr Asn Phe
            100                 105                 110

Val Val Glu Ile Pro Lys Glu Thr Ser Ala Lys Met Glu Val Ala Thr
        115                 120                 125

Glu Glu Pro Ser Thr Pro Ile Lys Gln Asp Thr Lys Lys Gly Lys Leu
    130                 135                 140

Arg Phe Tyr Pro Tyr Asn Ile Asn Trp Asn Tyr Gly Leu Leu Pro Gln
145                 150                 155                 160
```

-continued

```
Thr Trp Glu Asp Pro Ser His Ser Asn Ser Asp Val Glu Asn Ala Phe
            165                 170                 175
Gly Asp Asn Asp Pro Val Asp Val Val Glu Ile Gly Glu Arg Gln Ala
        180                 185                 190
Lys Ile Gly Glu Val Leu Lys Val Lys Pro Ile Ala Val Leu Ala Met
    195                 200                 205
Ile Asp Glu Gly Glu Leu Asp Trp Lys Val Val Ala Ile Ser Ile Asp
210                 215                 220
Asp Pro Lys Ala Asp Leu Val Asn Asn Val Ala Asp Cys Glu Lys His
225                 230                 235                 240
Phe Pro Gly Thr Leu Thr Ala Ile Arg Asp Trp Phe Arg Asp Tyr Lys
            245                 250                 255
Ile Pro Asp Gly Lys Pro Ala Asn Arg Phe Gly Leu Asp Asn Lys Pro
        260                 265                 270
Ala Asp Lys Asp Tyr Ala Leu Lys Val Ile Glu Glu Thr Asn Asn Ala
    275                 280                 285
Trp Ala Asn Leu Val Lys Arg Ser Val Pro Ala Gly Glu Leu Ser Leu
290                 295                 300
Val
305
```

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 4
caggaaacag ctatgacc                                                   18

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 5
ctaaagggaa caaaagctg                                                  19

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 6
tgtaaaacga cggccagt                                                   18

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 7
atcccgggtg acaatggcgg cagcaagagc t                                    31

```
<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 8
atgagctcac actaaactct agcaaaactg aag                                    33

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 9
gaatagatac gctgacacgc                                                   20

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 10
atgagctcac actaaactct agcaaaactg aag                                    33

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 11
gcagagtata ccgtcaagga ggaag                                             25

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 12
ggcttgcctc tccccaattt caaca                                             25
C:\®esults[1]6313006 (4).DOC
```

We claim:

1. An isolated nucleic acid encoding a polypeptide, wherein the nucleic acid comprises a polynucleotide selected from the group consisting of:
   a). a polynucleotide as defined in SEQ ID NO:2; and
   b). a polynucleotide encoding a polypeptide as defined in SEQ ID NO:3.

2. The isolated nucleic acid of claim 1, wherein the nucleic acid comprises the polynucleotide as defined in SEQ ID NO:2.

3. The isolated nucleic acid of claim 1, wherein the nucleic acid encodes the polypeptide as defined in SEQ ID NO:3.

4. The isolated nucleic acid of claim 1, wherein the nucleic acid confers tolerance to drought stress when transformed into a plant as compared to a wild type variety of the plant.

5. The isolated nucleic acid of claim 4, wherein the plant is a monocot.

6. The isolated nucleic acid of claim 4, wherein the plant is a dicot.

7. The isolated nucleic acid of claim 4, wherein the plant is selected from the group consisting of maize, wheat, rye, oat, triticale, rice, barley, soybean, peanut, cotton, rapeseed, canola, manihot, pepper, sunflower, tagetes, solanaceous plants, potato, tobacco, eggplant, tomato, *Vicia* species, pea, alfalfa, coffee, cacao, tea, *Salix* species, oil palm, coconut, and perennial grass.

8. A method of producing a transgenic plant having increased tolerance to drought stress as compared to a wild type variety of the plant, the method comprising the steps of, transforming a plant cell with an expression vector that increases expression of a transgene, and generating from the plant cell a transgenic plant with an increased tolerance to drought stress as compared to a wild type variety of the plant, wherein the transgene is selected from the group consisting of:
 a). a polynucleotide as defined in SEQ ID NO:2; and
 b). a polynucleotide encoding a polypeptide as defined in SEQ ID NO:3.

9. The method of claim 8, wherein the polynucleotide is defined in SEQ IDNO:2.

10. The method of claim 8, wherein the polynucleotide encodes the polypeptide as defined in SEQ ID NO:3.

11. The method of claim 8, wherein the plant is a monocot.

12. The method of claim 8, wherein the plant is a dicot.

13. The method of claim 8, wherein the plant is selected from the group consisting of maize, wheat, rye, oat, triticale, rice, barley, soybean, peanut, cotton, rapeseed, canola, manihot, pepper, sunflower, tagetes, solanaceous plants, potato, tobacco, eggplant, tomato, *Vicia* species, pea, alfalfa, coffee, cacao, tea, *Salix* species, oil palm, coconut, and perennial grass.

* * * * *